(12) United States Patent
Shin et al.

(10) Patent No.: US 8,846,368 B2
(45) Date of Patent: *Sep. 30, 2014

(54) BACTERIOPHAGE AND ANTIBACTERIAL COMPOSITION COMPRISING THE SAME

(71) Applicant: CJ Cheiljedang Corporation, Seoul (KR)

(72) Inventors: Soo An Shin, Seoul (KR); Min Tae Park, Seoul (KR); Hyang Choi, Anyang-si (KR); Young Wook Cho, Seoul (KR); In Hye Kang, Suwon-si (KR); Su Jin Choi, Daegu (KR)

(73) Assignee: CJ Cheiljedang Corporation, Seoul (KR)

( * ) Notice: Subject to any disclaimer, the term of this patent is extended or adjusted under 35 U.S.C. 154(b) by 4 days.

This patent is subject to a terminal disclaimer.

(21) Appl. No.: 13/621,688

(22) Filed: Sep. 17, 2012

(65) Prior Publication Data

US 2014/0017205 A1    Jan. 16, 2014

Related U.S. Application Data

(63) Continuation-in-part of application No. 12/875,863, filed on Sep. 3, 2010, now Pat. No. 8,293,515.

(60) Provisional application No. 61/239,751, filed on Sep. 3, 2009.

(51) Int. Cl.
| | | |
|---|---|---|
| *C12N 7/00* | (2006.01) | |
| *A01N 63/00* | (2006.01) | |
| *A61K 35/76* | (2006.01) | |

(52) U.S. Cl.
CPC ........ *C12N 7/00* (2013.01); *C12N 2795/10351* (2013.01); *C12N 2795/10331* (2013.01); *C12N 2795/10371* (2013.01); *C12N 2795/10311* (2013.01); *A01N 63/00* (2013.01); *A61K 35/76* (2013.01); *C12N 2795/10321* (2013.01); *C12N 2795/10332* (2013.01)
USPC ........................................ 435/235.1; 435/239

(58) Field of Classification Search
None
See application file for complete search history.

(56) References Cited

U.S. PATENT DOCUMENTS

| 6,485,902 B2 | 11/2002 | Waddell et al. |
| 6,942,858 B1 | 9/2005 | Ghanbari et al. |
| 2004/0208853 A1 | 10/2004 | Sulakvelidze et al. |

OTHER PUBLICATIONS

Zoonoses Report, 2003, pp. 1-71, United Kingdom.
Al-Tarazi, et al. Asian-Aust. J. Anim. Sci., 2003, 16(1):77-82.
Raya, et al. Applied and Environmental Microbiology, 1982, 55(9):2206-2213.
O'Flynn, et al. Journal of Applied Microbiology, 2006, 101:251-259.
Barrangou, et al. Applied and Environmental Microbiology, 2002, 68(11):5452-5458.
Goto, et al. J. Food Hyg. Soc. Japan, 2004, 45(1):25-28.

*Primary Examiner* — Nicole Kinsey White
(74) *Attorney, Agent, or Firm* — Seed IP Law Group PLLC

(57) ABSTRACT

Disclosed herein is a novel bacteriophage which has specific bactericidal activity against one or more *Salmonella* bacteria selected from the group consisting of *Salmonella enteritidis, Salmonella typhimurium, Salmonella gallinarum*, and *Salmonella pullorum* without affecting beneficial bacteria, in addition to showing excellent tolerance to acid, heat and desiccation. The novel bacteriophage of the present invention can be widely used as an active ingredient for therapeutic agents, animal feeds or drinking water, cleaners and sanitizers for preventing and treating the infectious diseases caused by *Salmonella enteritidis, Salmonella typhimurium, Salmonella gallinarum* or *Salmonella pullorum* including salmonellosis, *Salmonella* food poisoning, Fowl Typhoid, and Pullorum disease or for controlling the *Salmonella* bacteria. The present invention also provides important insights into prevention and control strategies against *Salmonella* infection and suggests that the use of bacteriophage can be a novel, safe, and effectively plausible alternative to antibiotics for the prevention of *Salmonella* infection in poultry.

2 Claims, 6 Drawing Sheets

SEQUENCE LISTING

```
<160> NUMBER OF SEQ ID NOS: 20

<210> SEQ ID NO 1
<211> LENGTH: 1029
<212> TYPE: DNA
<213> ORGANISM: Bacteriophage KCCM11027P

<400> SEQUENCE: 1
atctcctcaa cataggcaac gttaacttcg ccggggcgat ggctgaccag gctaataccc      60
tgaacggagc tatcgctagt gcggaggact catggtccca gttgaagatg actctcgcta     120
ctagtctgga tgtagggtcg ctggcggaac ctttacgtta tattgacgac ctgatacagg     180
agataaacgc tcaggtcgca tccggtgagt tcgtagccga gatgcagatg tggggtgaca     240
tggcatccga tgttgggggt gcgatagagg cttcattcga cgcggcgttt gggacggttg     300
cagacgcgtt aaacgctttg aactccgcct ggacttacac cagtgaaagc attaccggaa     360
gcggagagga gaccgcatct acgatagctg agtcggcggc ggatgcgctg gacttcattg     420
cccaggaatt tacagcaatg gagcggtttt ttgaagatat ggttaaaggt gctcaggatg     480
caggacgtct tgtaaaggcc gccttgacgc cgggagagtc ggtagctgag gccaagaacc     540
ttaacttcca gttagcgctt gctatggata ctcaaagggg tgtggctgac ctgacacgga     600
aaagtttccg cgaacaagta gaagctcagg aagaccttat tgcgctgaag cgagcggctt     660
acgacatcga tgaagaagca gctaaggccg aggggttagg taagtttaag gtatcaggta     720
cggacagcgg ttctacaggt gattccgcag acaaggccgc taagaaatcc gtcgacgcat     780
tcgaacgcca gaagaaagcc gctgaggatt tctattatca gtcaatccac cttaacgacg     840
```

```
acgtattcca gagatacaag ctaaccaaga agagcaactt acaaagctac aggagttcta      900
cagcaaccgt ctccttagtg accagcatac gaaaccgcga agacgcagat tatgctcgag      960
gcggatacgg ccgccaggct gagtagataa cgcgagaaag aacgctggaa aaacagttct     1020
cgcgatgcg                                                             1029

<210> SEQ ID NO 2
<211> LENGTH: 741
<212> TYPE: DNA
<213> ORGANISM: Bacteriophage KCCM11027P

<400> SEQUENCE: 2
cgaacgccgt cgtaaccgtt aatatatttt cttttcaatt aaggcggctt cggtcgcctt       60
ttctataagg gtcaaataaa tgaatctgct ttatctcgat actgaaacat tttcagaagc      120
cgatttaaaa aaagtcggtt cctatgctta cgccgaacat ccgactaccg aaattgttat      180
ctgcacctac gctttcgatg aaggccctgt gcaagtatgg gacgccaccg acggcagcga      240
tatgccgcgt gatttgcgtc gggcgatgtt gaagctgcaa aaaccagaca gcaatctcaa      300
actggtaggc caaaacttcc ttatgttcga ccgaccagtt attaagcatt gctgggggtt      360
cgaactcctg gtagaaaaca ttatagacac tatgatagta gcgttccgac atgccctccc      420
gggttcactg gccgcgctgt gtgaggtttt aaacattgac gcaagcatgg ctaaggataa      480
acgtggtaag gcgctgatac agcgattcag taagcctacg cccaagaact ataagattcg      540
acgttatact gccgataccc acccaaaaga gtgggcagaa tttattgcat acgcaaaaag      600
cgactttacg tccatgcgtg aagtgtataa gaaaatgcct aactgggtga attctgagtt      660
cgaaaaccgc gtgcggcact taaacggggc gattaattac cgaggattaa aggtgttgtg      720
gctttgctgg aagcggtaaa g                                                741

<210> SEQ ID NO 3
<211> LENGTH: 997
<212> TYPE: DNA
<213> ORGANISM: Bacteriophage KCCM11027P

<400> SEQUENCE: 3
atctcctcaa cataggcaac gttaacttcg ccggggcgat ggctgaccag gctaataccc       60
tgaacggagc tatcgctagt gcggaggact catggtccca gttgaagatg actctcgcta      120
ctagtctgga tgtagggtcg ctggcggaac ctttacgtta tattgacgac ctgatacagg      180
agataaacgc tcaggtcgca tccggtgagt tcgtagccga gatgcagatg tggggtgaca      240
tggcatccga tgttgggggt gcgatagagg cttcattcga cgcggcgttt gggacggttg      300
cagacgcgtt aaacgctttg aactccgcct ggacttacac cagtgaaagc attaccggaa      360
gcggagagga gaccgcatct acgatagctg agtcggcggc ggatgcgctg gacttcattg      420
cccaggaatt tacagcaatg gagcggtttt tgaagatat ggttaaaggt gctcaggatg      480
caggacgtct tgtaaaggcc gccttgacgc cgggagagtc ggtagctgag gccaagaacc      540
ttaacttcca gttagcgctt gctatggata ctcaaagggg tgtggctgac ctgacacgga      600
aaagtttccg cgaacaagta gaagctcagg aagacctttat tgcgctgaag cgagcggctt      660
acgacatcga tgaagaagca gctaaggccg aggggttagg taagtttaag gtatcaggta      720
cggacagcgg ttctacaggt gattccgcag acaaggccgc taagaaatcc gtcgacgcat      780
tcgaacgcca gaagaaagcc gctgaggatt tctattatca gtcaatccac cttaacgacg      840
```

| | |
|---|---|
| acgtattcca gaagatacaa gctaaccaag agagcaactt acaaagctac aggagttcta | 900 |
| cagcaaccgt ctccttagtg accagcaata cgaaaccgcg aagacgcaga tatgcctcga | 960 |
| ggcggatacg gccgccaggc tgagttagat aacgcga | 997 |

```
<210> SEQ ID NO 4
<211> LENGTH: 969
<212> TYPE: DNA
<213> ORGANISM: Bacteriophage KCCM11027P

<400> SEQUENCE: 4
```

| | |
|---|---|
| aacggtctca ttgttgctga agttgtaatc gcggtcgata agaacactat caacagcggc | 60 |
| atccgccaat cgttgtaacg tagtaaagtc agacagctta acggagtact taaatttctt | 120 |
| atccgcttcc gcacggaagg tgatgtcccc aaaagctacc caagcagaat cagaaatgcc | 180 |
| accggttgtt agaggggtag acgccgcggg ataactttc ggcagggagc cacgccatgc | 240 |
| gtaatagtta ccgtccccgc catcttcttt cggccaaaga accgctttat tggcgtcgtt | 300 |
| aattcccagg gttccgccgg ttgtgaagtt aaaagacgcc ggagagaaac cggcgtcacg | 360 |
| caagaccgcg ggcagcgtct tctgcgtctg cccggttacc tggttagtag cgtagtcgat | 420 |
| atctgcgcca cccgctacac caccctgtct gccggtgatc acctcggctt cgaaaatctg | 480 |
| gtgttttta gctacctgta aatcgtaaag tgacaataca tcaccgcaac cactagacat | 540 |
| atgactatcc tcttagttaa aaccgttatc gaatccgtta gagaacgcac gaccgaaagg | 600 |
| cggtacgttg tcgaacttat agaaatcctt gtcatagtta aacccggtta ttttgactgt | 660 |
| tctgtcatcg ccggggtcta ccgtagaaac aagaatcatc tgagcattat gccttgcttc | 720 |
| gttgccgaat gaaaattcag ttttcagggc gctattaccc gtgtaaatgg cttcctgcgg | 780 |
| tacagaagtc ataatcaccc gcctgtcgtg cgctccaggg actacattaa cactttgcac | 840 |
| gccgccgtca cgtaacttga gaatcaaaga atggtcatct cccgaggtga acttaactgg | 900 |
| gttgtgacag ttctacgtga gcccgtttac cgcggttacg tagccgtcgt agtcgcatac | 960 |
| gtgaaccct | 969 |

```
<210> SEQ ID NO 5
<211> LENGTH: 918
<212> TYPE: DNA
<213> ORGANISM: Bacteriophage KCCM11027P

<400> SEQUENCE: 5
```

| | |
|---|---|
| gacgtagaga taataggaca ctattaacgg ttatgcaagc tattttgtta ttcttatttg | 60 |
| gcgtctacgg tcgcaccgga aaagcgggtg gttcccgcct ggtgcaacta ccaaccagta | 120 |
| accgactaac caaagggcat tactatgaaa cttagcgatt tttactacga agccgaagcc | 180 |
| gagaaaggcg cgcgcatgcc gattcctta aaagatggta cagattcagg agaatggttg | 240 |
| aacgttgtct ccccggaggc cgatgtcgcg gttaaagcta tgcgtgcctt caccctggcg | 300 |
| taccgagcgg cggtaggtaa attaaaaccg cttcggata aatgcgaaga gcaaaaagac | 360 |
| ttctcagaat acaatttaaa aatggaagac gcggcaggag acctaaaccg acaattggct | 420 |
| ctcgaattgg tgaatggctg gagtctcgat gatgagttca ctaaggaaaa tcttaagact | 480 |
| cttctcaccc aatataagcg cctggcggaa catgtagtcg tattccacca cgaacagttg | 540 |
| cgtcaattgc aggaaaagta gacgcgttgt tcagtttgc ccgttggaac ttcataaccc | 600 |
| gccacgaaag gcgcaagttt gacagtatcg ccgatgggca caaagccgcg cttatcgcta | 660 |
| tgggggtaat aaaagacgcg ggagaaacaa cgcaggacgc cgggcctgaa tgccccctg | 720 |

```
aactactcac cactttgag aagtatcgtg atgttaaatt cacccgccgc gttgatgacg    780
acggcgtaaa gctataccca agagagcaac ttagttggtc agattagtg gcgtatagca    840 ctatttcagg tcagatatag ggatgtttga atctgaaatt atcatgggct tagacgccat    900
ttttgagggt agaaacga                                                  918

<210> SEQ ID NO 6
<211> LENGTH: 1004
<212> TYPE: DNA
<213> ORGANISM: Bacteriophage KCCM11027P

<400> SEQUENCE: 6
aacttatacg ggcaaacacg tgacaacacc ccacactacg gcaacagaac aacagtacac     60
tcgatgcgca agcagacccc acgtgctgcg gaagtaaagc aaccacagtt acgtatgatt    120
gccaccgaaa tggtacacaa ataccttggt aacggtgttt tcgaagatac gatgaccccc    180
aatacccagg ccgtgcaatc tcttatccgc ctggcgcgtg atccggatgt gggggggttta   240 aacctgacgg tacgcaacat ggataagtta cttgccgtgc agaacgaggt cgaagcgtat    300
ttcggtgaca acaggctgg agaattttgt tacacgtttg atgactataa aaccactatg     360
caggatatag ttagtactat agccgacgct atcttctgta ctccatatag gcgtggggcg    420
gatatccttc tcgattttga acgccctcgc atgggccctg agatggtgtt cacccaccga    480
agcaaggctg gtacttccga aaatggacc agaacctta acgatgctca ggtgttcgat       540
agccttaaat tctcgtacat agacccaaaa acaaacgtta agaaacaat aacaatacca      600 gaaactggtg gggttaaaac ggagacctac gattcaaaag gtattcgcaa ctataagcag    660
gctttctggg cagcgcaccg ccgccaccag aagaacattt taagaaaat ttcagtgtcg     720 tttaccgcca cggaagaggg tatctttgct ttaccaaatc gtgccattag tgtggttaag   780
ggttcacgta tggcgaccta cgacggctac gtaaccgcgg taaacgggct caccgtagaa    840
ctgtcacaac cagttaagtt cacctcggga gatgaccatt ctttgattct caagttacgt    900
gacggcggcg tgcaaagtgt taatgtagtc cctggagcgc acgacaggcg ggtgattatg    960
acttctgtac cgcaggaagc catttacacg ggtatagcgc cctg                    1004

<210> SEQ ID NO 7
<211> LENGTH: 18
<212> TYPE: DNA
<213> ORGANISM: Artificial Sequence
<220> FEATURE:
<223> OTHER INFORMATION: synthesized

<400> SEQUENCE: 7
cctgaacgga gctatcgc                                                   18

<210> SEQ ID NO 8
<211> LENGTH: 20
<212> TYPE: DNA
<213> ORGANISM: Artificial Sequence
<220> FEATURE:
<223> OTHER INFORMATION: synthesized

<400> SEQUENCE: 8
ggagacggtt gctgtagaac                                                 20

<210> SEQ ID NO 9
<211> LENGTH: 20
<212> TYPE: DNA
```

<213> ORGANISM: Artificial Sequence
<220> FEATURE:
<223> OTHER INFORMATION: synthesized

<400> SEQUENCE: 9 atctgctttaa tctcgatact					20

<210> SEQ ID NO 10
<211> LENGTH: 18
<212> TYPE: DNA
<213> ORGANISM: Artificial Sequence
<220> FEATURE:
<223> OTHER INFORMATION: synthesized

<400> SEQUENCE: 10
cccgtttaag tgccgcac					18

<210> SEQ ID NO 11
<211> LENGTH: 18
<212> TYPE: DNA
<213> ORGANISM: Artificial Sequence
<220> FEATURE:
<223> OTHER INFORMATION: synthesized

<400> SEQUENCE: 11
tcctcaacat aggcaacg					18

<210> SEQ ID NO 12
<211> LENGTH: 20
<212> TYPE: DNA
<213> ORGANISM: Artificial Sequence
<220> FEATURE:
<223> OTHER INFORMATION: synthesized

<400> SEQUENCE: 12
aggagacggt tgctgtagaa					20

<210> SEQ ID NO 13
<211> LENGTH: 19
<212> TYPE: DNA
<213> ORGANISM: Artificial Sequence
<220> FEATURE:
<223> OTHER INFORMATION: synthesized

<400> SEQUENCE: 13
aacggtctca ttgttgctg					19

<210> SEQ ID NO 14
<211> LENGTH: 18
<212> TYPE: DNA
<213> ORGANISM: Artificial Sequence
<220> FEATURE:
<223> OTHER INFORMATION: synthesized

<400> SEQUENCE: 14
gacggctacg taaccgcg					18

<210> SEQ ID NO 15
<211> LENGTH: 19
<212> TYPE: DNA
<213> ORGANISM: Artificial Sequence
<220> FEATURE:
<223> OTHER INFORMATION: synthesized

<400> SEQUENCE: 15 gattcctttaa aaagatggt					19

```
<210> SEQ ID NO 16
<211> LENGTH: 18
<212> TYPE: DNA
<213> ORGANISM: Artificial Sequence
<220> FEATURE:
<223> OTHER INFORMATION: synthesized

<400> SEQUENCE: 16
atggcgtcta agcccatg                                                 18

<210> SEQ ID NO 17
<211> LENGTH: 20
<212> TYPE: DNA
<213> ORGANISM: Artificial Sequence
<220> FEATURE:
<223> OTHER INFORMATION: synthesized

<400> SEQUENCE: 17
ccacactacg gcaacagaac                                               20

<210> SEQ ID NO 18
<211> LENGTH: 19
<212> TYPE: DNA
<213> ORGANISM: Artificial Sequence
<220> FEATURE:
<223> OTHER INFORMATION: synthesized

<400> SEQUENCE: 18
cgccgtcacg taacttgag                                                19

<210> SEQ ID NO 19
<211> LENGTH: 19
<212> TYPE: DNA
<213> ORGANISM: Artificial Sequence
<220> FEATURE:
<223> OTHER INFORMATION: synthesized

<400> SEQUENCE: 19
cgggcctctt cgctattac                                                19

<210> SEQ ID NO 20
<211> LENGTH: 20
<212> TYPE: DNA
<213> ORGANISM: Artificial Sequence
<220> FEATURE:
<223> OTHER INFORMATION: synthesized

<400> SEQUENCE: 20
aggcttaccc gtcttactgt                                               20
```

BACTERIOPHAGE AND ANTIBACTERIAL COMPOSITION COMPRISING THE SAME

CROSS-REFERENCE TO RELATED APPLICATIONS

The present application is a continuation-in-part of U.S. patent application Ser. No. 12/875,863, filed Sep. 3, 2010, now U.S. Pat. No. 8,293,515, which claims priority to U.S. Provisional Application No. 61/239,751, filed Sep. 3, 2009. The above applications are incorporated herein by reference.

REFERENCE TO SEQUENCE LISTING

The material in the ASCII text filed submitted on Sep. 26, 2013, is incorporated herein by reference. The ACSII text file is named "hanol5.005p1_seq 1st_2013-09-04. txt", created Sep. 4, 2013 and is 11 kilobytes in size.

TECHNICAL FIELD

The present invention relates to a novel bacteriophage, a composition comprising the bacteriophage, and a method for preventing infectious diseases caused by *Salmonella* using the bacteriophage.

BACKGROUND ART

*Salmonella* is a genus of the family Enterobacteriaceae, characterized as Gram-negative, facultatively anaerobic, non spore-forming, rod-shaped bacteria, and most strains are motile by flagella. *Salmonella* has an average genomic GC content of 50-52%, which is similar to that of *Escherichia coli* and *Shigella*. The genus *Salmonella* is a pathogenic microorganism that causes infections in livestock as well as in humans. Serological division has it that *Salmonella enterica*, a species of *Salmonella* bacterium, has a variety of serovars including *Gallinarum, Pullorum, Typhimurium, Enteritidis, Typhi, Choleraesuis*, and derby (Bopp C A, et al., eds. *Manual of Clinical Microbiology*. 7th ed. Washington D.C. American Society for Microbiology 1999; 467-74; Ryan K J. Ray CG (editors) (2004). *Sherris Medical Microbiology* (4th ed). McGraw Hill. ISBN 0-8385-8529-9.). Of them, *Salmonella gallinarum* and *pullorum* are fowl-adapted pathogens, *Salmonella typhi* is a human-adapted pathogen, *Salmonella choleraesuis* and *Salmonella* derby are swine-adapted pathogens, and *Salmonella enteritis* and *Salmonella typhimurium* are pathogenic for humans and animals. Each serovar causes illness in the respective species, resulting in tremendous damage to farmers or consumers.

A disease of domestic birds caused by *Salmonella* bacterium is Fowl Typhoid (FT), which is caused by a pathogen, *Salmonella gallinarum* (hereinafter, referred to as "SG"). Fowl Typhoid (FT) is a septicemic disease of domestic birds such as chicken and turkey, and the course may be acute or chronic with high mortality. A recent report has had it that Fowl Typhoid frequently occurs in Europe, South America, Africa, and Southeast Asia, with damages increasing every year. Outbreaks of FT in South Korea have been reported since 1992 and economic losses caused by FT in brown, egg-laying chickens are very serious (Kwon Yong-Kook. 2000 annual report on avian diseases. Information publication by National Veterinary Research & Quarantine Service. March, 2001; Kim Ae-Ran et al., The prevalence of *pullorum* disease-fowl typhoid in grandparent stock and parent stock in Korea, 2003, Korean J Vet Res (2006) 46(4): 347-353).

*Pullorum* disease is also caused by a strain of the *Salmonella* bacteria, *Salmonella pullorum* (hereinafter, referred to as "SP"). *Pullorum* disease occurs in any age or season, but young chickens are particularly susceptible to the disease. During the past century, it has been a serious disease among young chickens at 1-2 weeks of age or younger. Since the 1980s, the occurrence has greatly decreased. However, it has been growing since the mid-1990s (Kwon Yong-Kook. 2000 annual report on avian diseases. Information publication by National Veterinary Research & Quarantine Service. March, 2001; Kim Ae-Ran et al., The prevalence of *pullorum* disease-fowl typhoid in grandparent stock and parent stock in Korea, 2003, Korean J Vet Res, 2006, 46(4): 347-353).

In South Korea, outbreaks of Fowl Typhoid and *Pullorum* disease have been increasing since the 1990s, inflicting economic damages on farmers. For this reason, a live attenuated SG vaccine has been used in broilers for the prevention of Fowl Typhoid from 2004 (Kim Ae-Ran et al., The prevalence of *pullorum* disease-fowl typhoid in grandparent stock and parent stock in Korea, 2003, Korean J Vet Res, 2006, 46(4): 347-353). Its efficacy is doubtful, and the live vaccine is not allowed to be used for layers because of the risk of egg-transmitted infections. Unfortunately, there are still no commercially available preventive strategies against *Pullorum* disease, unlike Fowl Typhoid. Thus, there is an urgent need for new ways to prevent Fowl Typhoid and *Pullorum* disease.

Meanwhile, *Salmonella enteritidis* (hereinafter, referred to as "SE") and *Salmonella typhimurium* (hereinafter, referred to as "ST") are zoonotic pathogens, which show no host specificity, unlike SG or SP (Zoobises Report; United Kingdom 2003).

SE and ST are causative of salmonellosis in poultry, pigs, and cattle. Salmonellosis, caused by *Salmonella* bacteria, is an acute or chronic infection of the digestive tract in livestock, and shows the major symptoms of fever, enteritis, and septicemia, occasionally pneumonia, arthritis, abortion, and mastitis. Salmonellosis occurs worldwide, and most frequently during the summer months (T. R. Callaway et al., J Anim Sci 2008, 86: E163-E172). In cattle, typical symptoms include loss of appetite, fever, dark brown diarrhea or bloody mucous in stool. The acute infection in calves leads to rapid death, and the infection during pregnancy leads to fetal death due to septicemia, resulting in premature abortion. In pigs, salmonellosis is characterized clinically by three major syndromes: acute septicemia, acute enteritis, and chronic enteritis. Acute septicemia occurs in 2-4-month-old piglets, and death usually occurs within 2-4 days after onset of symptoms. Acute enteritis occurs during the fattening period, and is accompanied by diarrhea, high fever, pneumonia, and nervous signs. Discoloration of the skin may occur in some severe cases. Chronic enteritis is accompanied by continuing diarrhea.

Once an outbreak of salmonellosis by SE and ST occurs in poultry, pigs, and cattle, it is difficult to cure only with therapeutic agents. The reasons are that *Salmonella* bacteria exhibit a strong resistance to various drugs and live in cells that are impermeable to antibiotics upon the occurrence of clinical symptoms. Up to now, there have been no methods for effectively treating salmonellosis caused by SE and ST, including antibiotics.

As in livestock, SE and ST cause infections in humans via livestock and their products, leading to *Salmonella* food poisoning. Intake of infected, improperly cooked livestock products (e.g., meat products, poultry products, eggs and by-products) infects humans. *Salmonella* food poisoning in humans usually involves the prompt onset of headache, fever, abdominal pain, diarrhea, nausea, and vomiting. The symptoms commonly appear within 6-72 hours after the ingestion of the organism, and may persist for as long as 4-7 days or even longer (NSW+HEALTH. 2008 Jan. 14.).

According to a report by the CDC (The Centers for Disease Control and Prevention, USA), 16% of human food poisoning outbreaks between 2005 and 2008 were attributed to *Salmonella* bacteria, with SE and ST responsible for 20% and 18% thereof, respectively. With respect to *Salmonella* food poisoning in humans between 1973 and 1984, the implicated food vehicles of transmission were reportedly chicken (5%), beef (19%), pork (7%), dairy products (6%), and turkey (9%). In 1974-1984, the bacterial contamination test on broilers during the slaughter process showed 35% or more of *Salmonella* incidence. In 1983, *Salmonella* was isolated in 50.6% of chicken, 68.8% of turkey, 60% of goose, 11.6% of pork, and 1.5% of beef. Further, a survey carried out in 2007 reported that *Salmonella* was found in 5.5% of raw poultry meat and 1.1% of raw pork. In particular, it was revealed that SE commonly originated from contaminated egg or poultry meat, and ST from contaminated pork, poultry meat, and beef (Centers for Disease Control and Prevention, CDC). For example, food poisoning caused by SE has rapidly increased in the US, Canada, and Europe since 1988, and epidemiological studies demonstrated that it was attributed to eggs or egg-containing foods (Agre-Food Safety Information Service (AGROS), Domestic and foreign food poisoning occurrence and management trend. 2008. 02). A risk assessment conducted by FAO and WHO in 2002 noted that the human incidence of salmonellosis transmitted through eggs and poultry meat appeared to have a linear relationship to the observed *Salmonella* prevalence in poultry. This means that, when reducing the prevalence of *Salmonella* in poultry, the incidence of salmonellosis in humans will fall (*Salmonella* control at the source; World Health Organization. International Food Safety Authorities Network (INFOSAN) Information Note No. 03/2007). Recently, fears about food safety have been spurred by outbreaks of *Salmonella* from products as varied as peanuts, spinach, tomatoes, pistachios, peppers and, most recently, cookie dough (Jane Black and Ed O'Keefe. Overhaul of Food Safety Rules in the Works. Washington Post Staff Writers Wednesday, Jul. 8, 2009).

For these reasons, *Salmonella* infections must be reported in Germany (§6 and §7 of the German law on infectious disease prevention, Infektionsschutzgesetz). Between 1990 and 2005 the number of officially recorded cases decreased from approximately 200,000 cases to approximately 50,000. It is estimated that every fifth person in Germany is a carrier of *Salmonella*. In the USA, there are approximately 40,000 cases of *Salmonella* infection reported each year.

Therefore, there is an urgent need to control SE and ST, which cause salmonellosis in livestock and humans. The collaborative efforts of USDA and FDA have developed a number of effective strategies to prevent salmonellosis that causes over 1 million cases of food-borne illness in the United States. Among them is a final rule, issued by the FDA, to reduce the contamination in eggs. The FDA will now require that egg producers test regularly for lethal *Salmonella* during egg production, storage and shipment. As a result, an estimated 79,000 illnesses and 30 deaths due to contaminated eggs will be avoided each year (Jane Black and Ed O'Keefe. Overhaul of Food Safety Rules in the Works. *Washington Post* Staff Writers Wednesday, Jul. 8, 2009). In Denmark, conservative estimates from a cost benefit analysis comparing *Salmonella* control costs in the production sector with the overall public health costs of salmonellosis suggest that *Salmonella* control measures saved Danish society US$ 14.1 million in the year 2001 (Salmonella control at the source. World Health Organization. International Food Safety Authorities Network (INFOSAN) Information Note No. 03/2007).

Meanwhile, bacteriophage is a specialized type of virus that infects and destroys only bacteria, and can self-replicate only inside host bacteria. Bacteriophage consists of genetic material in the form of single or double stranded DNA or RNA surrounded by a protein shell. Bacteriophages are classified based on their morphological structure and genetic material. There are three basic structural forms of bacteriophage according to morphological structure: an icosahedral (twenty-sided) head with a tail; an icosahedral head without a tail; and a filamentous form. Based on their tail structure, bacteriophages having icosahedral head and double-stranded, linear DNA as their genetic material are divided into three families: Myoviridae, Siphoviridae, and Podoviridae, which are characterized by contractile, long noncontractile, and short noncontractile tails, respectively. Bacteriophages having an icosahedral head without a tail and RNA or DNA as their genetic material are divided based on their head shape and components, and the presence of shell. Filamentous bacteriophages having DNA as their genetic material are divided based on their size, shape, shell, and filament components (H. W. Ackermann. Frequency of morphological phage descriptions in the year 2000; Arch Virol (2001) 146:843-857; Elizabeth Kutter et al. Bacteriophages biology and application; CRC press).

During infection, a bacteriophage attaches to a bacterium and inserts its genetic material into the cell. After this a bacteriophage follows one of two life cycles, lytic or lysogenic. Lytic bacteriophages take over the machinery of the cell to make phage components. They then destroy or lyse the cell, releasing new phage particles. Lysogenic bacteriophages incorporate their nucleic acid into the chromosome of the host cell and replicate with it as a unit without destroying the cell. Under certain conditions, lysogenic phages can be induced to follow a lytic cycle (Elizabeth Kutter et al. Bacteriophages biology and application. CRC Press).

After the discovery of bacteriophages, a great deal of faith was initially placed in their use for infectious-disease therapy. However, when broad spectrum antibiotics came into common use, bacteriophages were seen as unnecessary due to a specific target spectrum. Nevertheless, the misuse and overuse of antibiotics resulted in rising concerns about antibiotic resistance and harmful effects of residual antibiotics in foods (Cislo, M et al. Bacteriophage treatment of suppurative skin infections. Arch. Immunol. Ther. Exp. 1987.2:175-183; Kim sung-hun et al., Bacteriophage; New Alternative Antibiotics. Biological research information center (BRIC)). In particular, antimicrobial growth promoter (AGP), added to animal feed to enhance growth, is known to induce antibiotic resistance, and therefore, the ban of using antimicrobial growth promoter (AGP) has been recently introduced. In the European Union, the use of all antimicrobial growth promoters (AGPs) was banned from 2006. South Korea has banned the use of some AGPs from 2009, and is considering restrictions on the use of all AGPs in 2013-2015.

These growing concerns about the use of antibiotics have led to a resurgence of interest in bacteriophage as an alternative to antibiotics. Seven bacteriophages for control of *E. coli* O157:H are disclosed in U.S. Pat. No. 6,485,902 (Use of bacteriophages for control of *Escherichia coli* O157, issued in 2002). Two bacteriophages for control of various microorganisms are disclosed in U.S. Pat. No. 6,942,858 (issued to Nymox in 2005). Many companies have been actively trying to develop various products using bacteriophages. EBI food system (Europe) developed a food additive for preventing food poisoning caused by *Listeria monocytogenes*, named Listex-P100, which is the first bacteriophage product approved by the US FDA. A phage-based product, LMP-102 was also developed as a food additive against *Listeria monocytogenes*, approved as GRAS (Generally Regarded As Safe). In 2007, a phage-based wash produced by OmniLytics was developed to prevent *E. coli* O157 contamination of beef during slaughter, approved by USDA's Food Safety and Inspection Service (FSIS). In Europe, *Clostridium sporogenes* phage NCIMB 30008 and *Clostridium tyrobutiricum* phage NCIMB 30008 were registered as a feed preservative against *Clostridium* contamination of feed in 2003 and 2005, respectively. Such studies show that research into bacteriophages for use as antibiotics against zoonotic pathogens in livestock products is presently ongoing.

However, most of the phage biocontrol studies have focused on the control of *E. coli*, *Listeria*, and *Clostridium*. *Salmonella* is also a zoonotic pathogen, and damages due to this pathogen are not reduced. As mentioned above, since SE and ST exhibit multiple drug resistance, nationwide antimicrobial resistance surveillance has been conducted in South Korea under the Enforcement Decree of the Act on the Prevention of Contagious Disease (Executive Order 16961), Enforcement ordinance of the Act on the Prevention of Contagious Disease (Ministry of Health and Welfare's Order 179), and Organization of the National Institute of Health (Executive Order 17164). Accordingly, there is a need for the development of bacteriophages to control *Salmonella*.

DISCLOSURE

Technical Problem

Leading to the present invention, intensive and thorough research into bacteriophages, isolated from natural sources, which infect the poultry pathogen *Salmonella*, conducted by the present inventors, aiming to overcome the problems occurring upon the use of broad spectrum antibiotics, resulted in the finding that some of the isolated bacteriophages have a specific bactericidal activity against *Salmonella enteritidis* (SE), *Salmonella typhimurium* (ST), *Salmonella gallinarum* (SG) and *Salmonella pullorum* (SP) with no influences on beneficial bacteria, in addition to showing excellent acid- and heat-resistance and desiccation tolerance, as identified for the morphorlogical, biochemical and genetic properties thereof, and thus that the bacteriophages are effective in the prevention and treatment of *Salmonella enteritidis*- or *Salmonella typhimurium*-mediated diseases, such as livestock salmonellosis and *Salmonella* food poisoning, and *Salmonella gallinarum*- or *Salmonella pullorum*-mediated diseases, particularly, Fowl Typhoid and *Pullorum* disease. Also, the bacteriophage according to the present invention can be applied to various products for the control of *Salmonella* bacteria, including livestock feed additives, drinking water for livestock, barn sanitizers, and cleaners for meal products.

Technical Solution

It is an object of the present invention to provide a novel bacteriophage which has a specific bactericidal activity against one or more *Salmonella* bacteria selected from the group consisting of *Salmonella enteritidis*, *Salmonella typhimurium*, *Salmonella gallinarum*, and *Salmonella pullorum*.

It is another object of the present invention to provide a composition for the prevention or treatment of infectious diseases caused by one or more *Salmonella* bacteria selected from the group consisting of *Salmonella enteritidis*, *Salmonella typhimurium*, *Salmonella gallinarum*, and *Salmonella pullorum*, comprising the bacteriophage as an active ingredient.

It is a further object of the present invention to provide a livestock feed additive, drinking water for livestock, and a cleaner or a sanitizer, comprising the bacteriophage as an active ingredient.

It is still a further object of the present invention to provide a method for preventing or treating infectious diseases caused by one or more *Salmonella* bacteria selected from the group consisting of *Salmonella enteritidis*, *Salmonella typhimurium*, *Salmonella gallinarum*, and *Salmonella pullorum* using the composition comprising the bacteriophage as an active ingredient.

Advantageous Effects

Having a specific bactericidal activity against one or more *Salmonella* bacteria selected from the group consisting of *Salmonella enteritidis*, *Salmonella typhimurium*, *Salmonella gallinarum*, and *Salmonella pullorum*, in addition to showing excellent acid- and heat-resistance and desiccation tolerance, the novel bacteriophage of the present invention is effective for the prevention and treatment of infectious diseases caused by *Salmonella enteritidis*, *Salmonella typhimurium*, *Salmonella gallinarum*, or *Salmonella pullorum*, including salmonellosis, *Salmonella* food poisoning, Fowl Typhoid and *Pullorum* disease, and can also be used for the control of *Salmonella enteritidis*, *Salmonella typhimurium*, *Salmonella gallinarum*, and *Salmonella pullorum*.

BEST MODE

Figure 1:
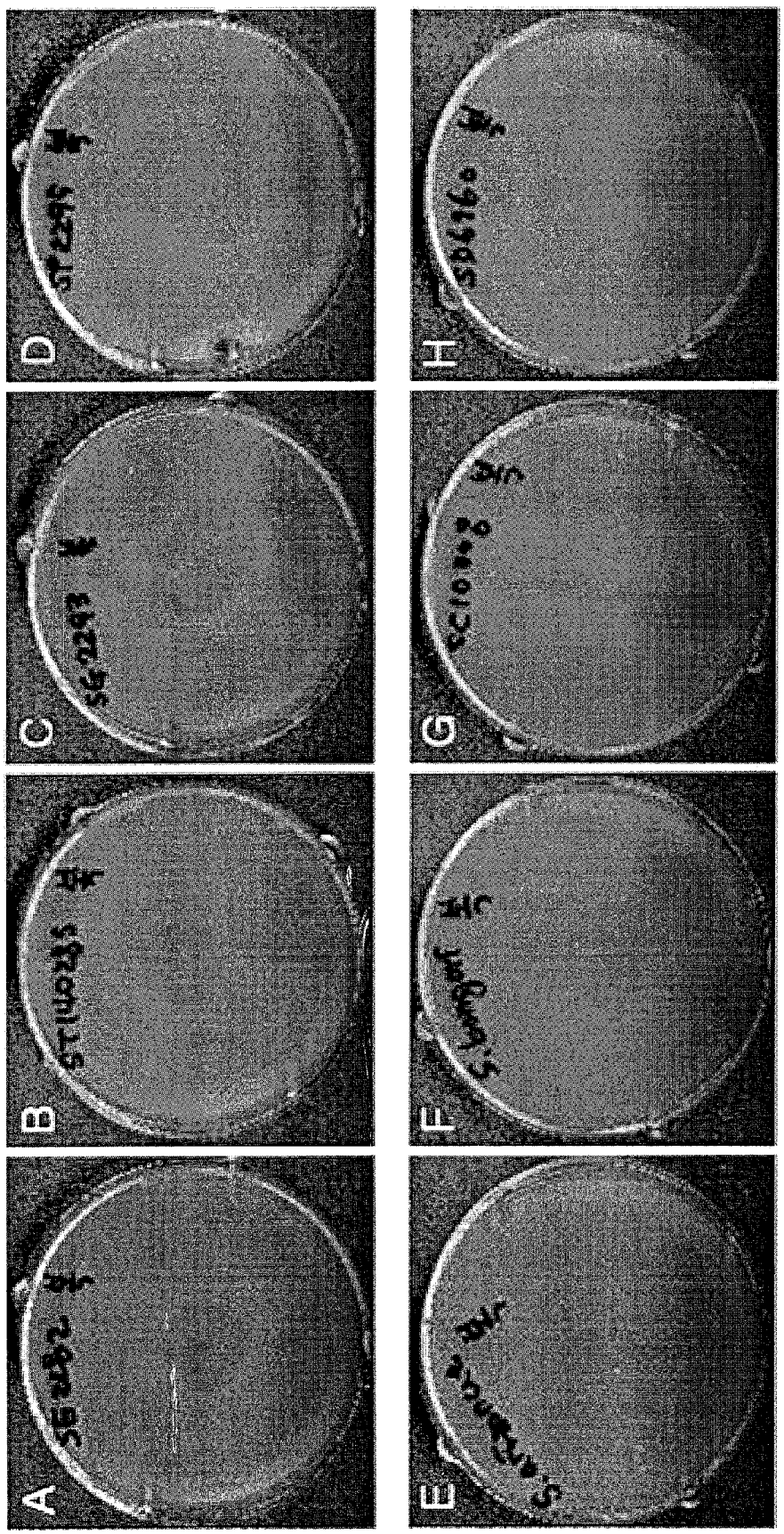
FIG. 1 is of photographs showing the formation of ΦCJ4 plaques in a lawn of *Salmonella* bacteria: A: in a lawn of SE; B: in a lawn of ST; C: in a lawn of SG; D: in a lawn of SP; E: in a lawn of SA; F: in a lawn of SB; G: in a lawn of SC; H: in a lawn of SD. Plaques formed in lawns of SE, ST, SG and SP, but not in lawns of SA, SB, SC and SD.

In accordance with an aspect, the present invention relates to a novel bacteriophage, belonging to a morphotype group of the family Siphoviridae, with a specific bactericidal activity against one or more *Salmonella* bacteria selected from the group consisting of *Salmonella enteritidis, Salmonella typhimurium, Salmonella gallinarum*, and *Salmonella pullorum*, characterized by one of the following properties: 1) the bacteriophage has a total genome size of 41-43 kb; 2) the bacteriophage contains as a part of the genome thereof at least one nucleotide sequence selected from among SEQ ID NOS.1 to 6; and 3) the bacteriophage has major structural proteins ranging in size from 39 to 41 kDa and from 16 to 18 kDa.

In a preferred embodiment, the bacteriophage of the present invention has a total genome size of about 42 kb, and structural proteins corresponding to respective sizes of about 69 kDa, about 40 kDa, about 38 kDa, about 17 kDa and about 14 kDa. Further, the bacteriophage may contain as parts of the genome thereof nucleic acid molecules of SEQ ID NOS. 1 to 6.

Also, the bacteriophage of the present invention has a morphological structure composed of an isometric capsid and a long, non-contractile tail.

The term "nucleic acid molecule", as used herein, is intended to include DNA (gDNA and cDNA) and RNA molecules. The term "nucleotides" which when joined together, make up the structural units of nucleic acid molecules, encompass natural ones and sugar- or base-modified analogues thereof.

Further, the bacteriophage of the present invention shows biochemical properties of being resistant to acid, heat and desiccation.

In greater detail, the bacteriophage of the present invention has excellent resistance to acid and heat so that it can survive over a wide pH range of from 3.5 to 11.0 and a heat range of from 37° C. to 70° C. With regard to the desiccation tolerance thereof, the bacteriophage can remain viable even under a high temperature and dry condition (e.g., 120 min at 60° C.). Thanks to the superiority thereof in resistance to acid, heat and desiccation, the bacteriophage of the present invention can be used in a wide range of temperature and pH, finding applications in compositions and products for the prevention and treatment of livestock diseases and livestock-mediated human diseases.

When PCR is performed in the presence of a primer set selected from among SEQ ID NOS. 7 and 8, SEQ ID NOS. 9 and 10, SEQ ID NOS. 11 and 12, SEQ ID NOS. 13 and 14, SEQ ID NOS. 15 and 16, and SEQ ID NOS. 17 and 18, with the genome of the bacteriophage of the present invention serving as a template, each PCR product is 500 bp-1,000 bp long. Preferably, PCR product is 500 bp-1,000 bp long, with the primer sets of SEQ ID NOS. 7 and 8, SEQ ID NOS. 9 and 10, SEQ ID NOS. 11 and 12, SEQ ID NOS. 13 and 14, SEQ ID NOS. 15 and 16, and SEQ ID NOS. 17 and 18.

The bacteriophage of the present invention which was isolated from sewage samples from chicken slaughterhouses and identified as having a specific bactericidal activity against SE, ST, SG and SP and the above characteristics, was designated as ΦCJ4 and deposited with the Korean Culture Center of Microorganisms (361-221, Honje 1, Seodaemun, Seoul) on Aug. 14, 2009 under accession number KCCM11027P.

Figure 2:
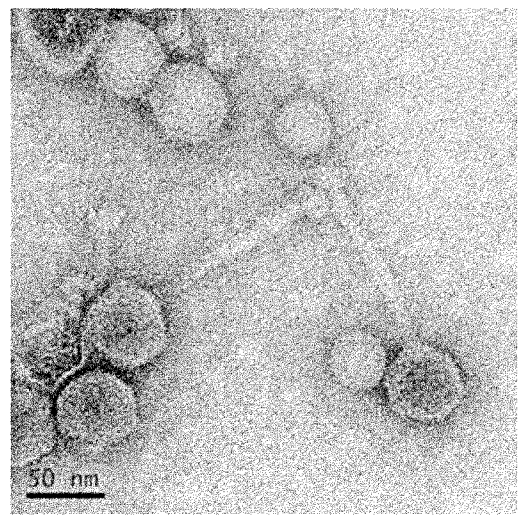
FIG. 2 is an electron microphotograph of ΦCJ4, showing that ΦCJ4 belongs to a morphotype group of the family Siphoviridae, characterized by an isometric capsid and a long non-contractile tail.

In accordance with an example of the present invention, sewage samples were collected from chicken slaughterhouses and used to isolate therefrom bacteriophages that can lyse the host cell SG. They were also found to lyse SE, ST, SG and SP (FIG. 1). An morphological examination under an electron microscope confirmed that the bacteriophage (ΦCJ4) belongs to a morphotype of the family Siphoviridae (FIG. 2).

Figure 3:
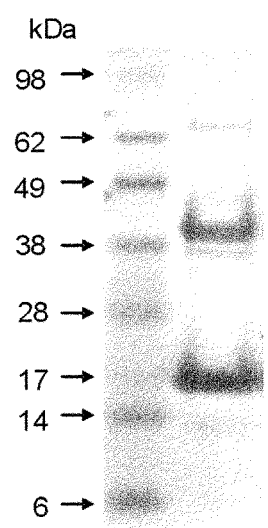
FIG. 3 is the result of SDS-PAGE of the isolated bacteriophage ΦCJ4, in which major bands were detected at approximately 40 kDa and 17 kDa and minor bands at approximately 69 kDa, 38 kDa and 14 kDa, with See-blue plus 2 prestained-standard (Invitrogen) serving as a size marker.

The bacteriophage ΦCJ4 of the present invention was found to have major structural proteins with the size of 40 kDa and 17 kDa, as measured by a protein pattern analysis (FIG. 3).

Figure 4:
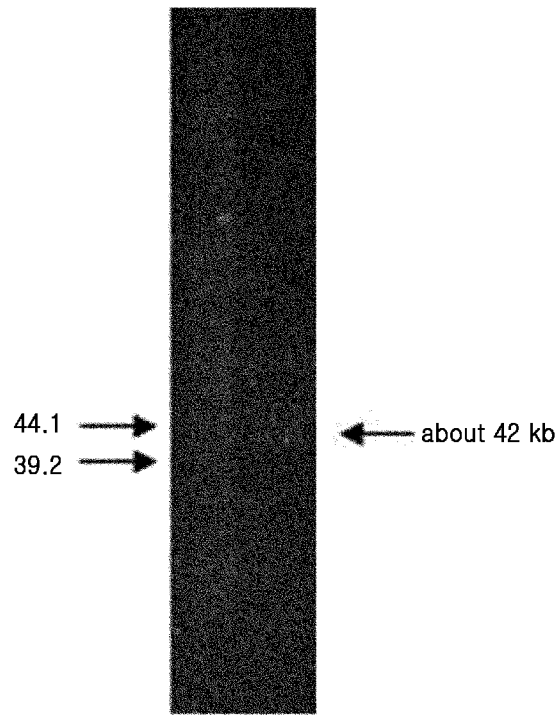
FIG. 4 is the result of PFGE of the isolated bacteriophage ΦCJ4, showing the total genome size of approximately 42 kb, with a 5 kbp DNA size standard (Bio-rad) serving as a size marker.
Figure 5:
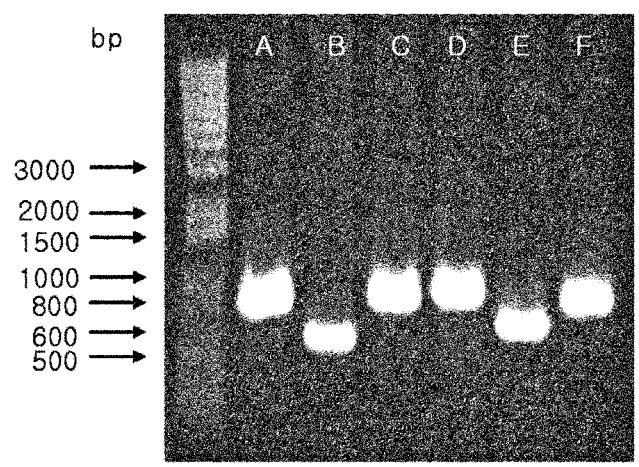
FIG. 5 is the result of PCR, performed using each primer set for the ΦCJ4 genomic DNA: A: a 860 bp-long PCR product obtained with a primer set of SEQ ID NOS. 7 and 8; B: a 600 bp-long PCR product obtained with a primer set of SEQ ID NOS. 9 and 10; C: a 900 bp-long PCR product obtained with a primer set of SEQ ID NOS. 11 and 12; D: a 950 bp-long PCR product obtained with a primer set of SEQ ID NOS. 13 and 14; E: a 700 bp-long PCR product obtained with a primer set of SEQ ID NOS. 15 and 16; F: a 880 bp-long PCR product obtained with a primer set of SEQ ID NOS. 17 and 18.

Further, a genome analysis showed that ΦCJ4 has a total genome size of approximately 42 kbp (FIG. 4), with the nucleic acid molecules of SEQ ID NOS. 1 to 6 incorporated thereinto. Also, the bacteriophage of the present invention was found to be of very low genetic similarity with known bacteriophages as measured by the comparison of genetic similarity with other species, indicating that the bacteriophage of the present invention is a novel one. More particularly, when PCR was performed using the primer sets SEQ ID NOS. 7 and 8, SEQ ID NOS. 9 and 10, SEQ ID NOS. 11 and 12, SEQ ID NOS. 13 and 14, SEQ ID NOS. 15 and 16, and SEQ ID NOS. 17 and 18, which were designed for ΦCJ4, the resulting PCR products were 860 bp, 600 bp, 900 bp, 950 bp, 700 bp, and 880 bp in size, respectively (FIG. 5).

Also, the phage plaques (clear zones formed in a lawn of cells on soft agar due to lysis by phage) resulting from the infection of ΦCJ4 into SE, ST, SG and SP were observed to have the same size and turbidity.

Figure 7:
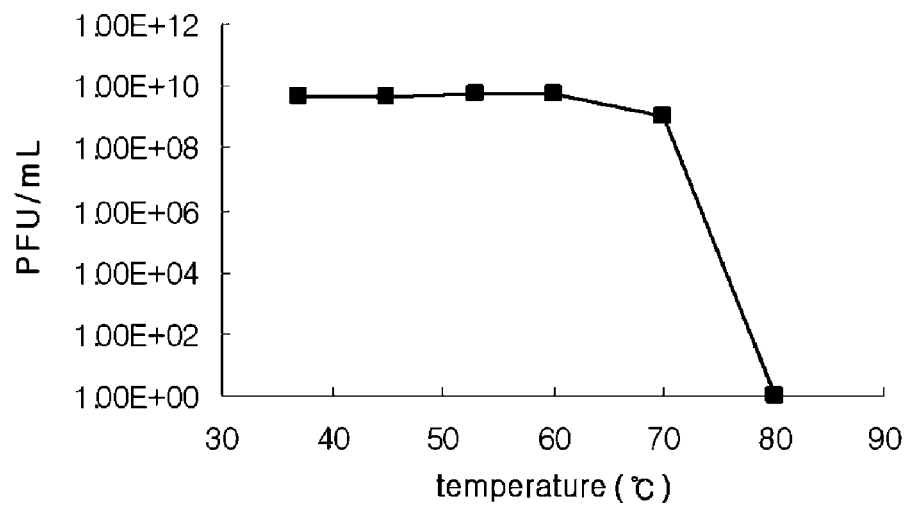
FIG. 7 is the result of heat-resistance assay on the bacteriophage ΦCJ4, showing the number of surviving bacteriophage at 37, 45, 53, 60, 70 and 80° C. for 120 min. The bacteriophage ΦCJ4 maintained its activity at up to 70° C.
Figure 8:
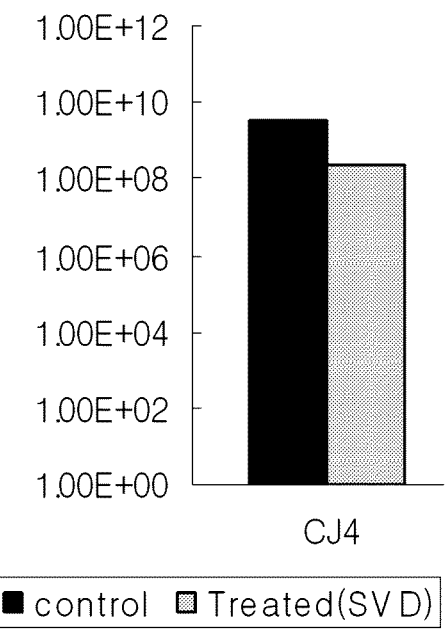
FIG. 8 is the result of desiccation resistance assay on the bacteriophage ΦCJ4, performed at 60° C. for 120 min with the aid of speed vacuum dryer (SVD), in which when titer changes under the dry condition were measured in comparison with pre-drying titers, the activity was decreased about 10-fold.

ΦCJ4 was examined for stability under a wide spectrum of pH, temperature, and desiccation. The bacteriophage was observed to survive over a pH range of from 3.0 to 11.0 (FIG. 6) and a temperature range of from 37° C. to 70° C. (FIG. 7) in addition to remaining stably viable even after desiccation at high temperature (60° C. for 120 min)(FIG. 8).

Also, the wild-type strains SE, ST, SG and SP were also found to fall within the host cell range of ΦCJ4.

When orally administered with ΦCJ4, rats were observed to remain unchanged in weight (FIG. 9), mortality, general symptoms and organ abnormality.

Also, a claning assay shows that the bacteriophage ΦCJ4 is found to have excellent bactericidal activity against *Salmonella* strains, compared to conventional cleaners as positive controls.

These data imply that the bacteriophage ΦCJ4 of the present invention can be applied to various products for the control of *Salmonella* bacteria.

In accordance with another aspect thereof, the present invention pertains to a composition for the prevention or treatment of infectious diseases caused by one or more *Salmonella* bacteria selected from the group consisting of *Salmonella enteritidis, Salmonella typhimurium, Salmonella gallinarum*, and *Salmonella pullorum*, comprising the bacteriophage as an active ingredient.

Preferably, examples of the infectious diseases include salmonellosis and *Salmonella* food poisoning by *Salmonella enteritidis* or *Salmonella typhimurium*, Fowl Typhoid by *Salmonella gallinarum* and *Pullorum* disease by *Salmonella pullorum* include, but are not limited thereto.

As used herein, the term "salmonellosis" refers to symptoms following *Salmonella* infection, such as fever, headache, diarrhea, and vomiting. That is, salmonellosis is an infection with bacteria of the genus *Salmonella*, with the accompaniment of two representative symptoms: septicemia such as typhoid fever; and acute gastroenteritis such as food poisoning, enteritis, and acute bacteremia.

Having a specific bactericidal activity against *Salmonella enteritidis, Salmonella typhimurium, Salmonella gallinarum* and *Salmonella pullorum*, the bacteriophage of the present invention can be used for preventing or treating diseases that are caused by the bacteria. In a preferred embodiment, the composition of the present invention may further comprise an antibiotic.

As used herein, the term "prevention" is intended to encompass all actions for restraining or delaying disease progress through the administration of the composition. The term "treatment" in this context encompasses all actions for improving or beneficially changing the patient's condition through the administration of the composition.

The composition of the present invention comprises ΦCJ4 in an amount of from $5\times10^2$ to $5\times10^{12}$ pfu/ml, and preferably in an amount of from $1\times10^6$ to $1\times10^{10}$ The composition of the present invention may further comprise a pharmaceutically acceptable vehicle, and may be formulated together with the carrier into foods, medicines, and feed additives.

As used herein, the term "pharmaceutically acceptable vehicle" refers to a carrier or diluent that neither causes significant irritation to an organism nor degrades the biological activity and properties of the administered active ingredient. For use in the formulation of the composition into a liquid preparation, a pharmaceutically acceptable vehicle must be suitable for sterilization and biocompatibility. Examples include saline, sterile water, Ringer's solution, buffered physiological saline, albumin infusion solution, dextrose solution, maltodextrin solution, glycerol, and ethanol. They may be used alone or in any combination thereof. If necessary, another conventional additive, such as antioxidants, buffers, bacteriostatic agents, etc., may be added to the composition. When combined additionally with diluents, dispersants, surfactants, binders and/and lubricants, the composition of the present invention may be formulated into injections such as aqueous solutions, suspensions and emulsions, or pills, capsules, granules, or tablets.

The prophylactic or therapeutic compositions of the present invention may be locally applied to afflicted areas by coating or spraying. Alternatively, the composition of the present invention may be administered through oral or parenteral routes. The parenteral routes are available for intravenous, intraperitoneal, intramuscular, subcutaneous or topical administration Depending on a variety of factors including formulations, the mode of administration, the age, weight, sex, condition and diet of the patient or animal being treated, the time of administration, the route of administration, the rate of excretion, and reaction sensitivity, the suitable dosage of the composition of the present invention will vary when it is applied, sprayed or administered. It will be apparent to those skilled in the art that when the pharmaceutical composition is administered to patients, the suitable total daily dose may be determined by an attending physician or veterinarian within the scope of sound medical judgment.

Oral dosage preparations of the composition of the present invention may take the form of tablets, troches, lozenges, aqueous or emulsive suspensions, powders or granules, emulsions, hard orsoft capsules, syrups, or elixirs. The oral dosage forms such as tablets and capsules may comprise a binder such as lactose, saccharose, sorbitol, mannitol, starch, amylopectin, cellulose or gelatin, an excipient such as dicalcium phosphate, a disintegrant such as corn starch or sweet potato starch, a lubricant such as magnesium stearate, calcium stearate, sodium stearylfumarate, or polyethylene glycol wax. For capsules, a liquid vehicle such as lipid may be further used.

For non-oral administration, the composition of the present invention may be formulated into injections via subcutaneous, intravenous, or intramuscular routes, suppositories, or sprays inhalable via the respiratory tract, such as aerosols. Injection forms may be prepared by dissolving or suspending the composition of the present invention, together with a stabilizer or a buffer, in water and loading the solution or suspension onto ampules or vial unit forms. For sprays, such as aerosols, a propellant for spraying a water-dispersed concentrate or wetting powder may be used in combination with an additive.

The term "antibiotic", as used herein, refer to a substance or compound that can be administered to animals to kill bacteria or inhibit their growth and is intended to encompass antiseptics, bactericidal agents and antibacterial agents. The animals are mammals including humans. Thanks to the advantage of being of higher specificity for *Salmonella* over conventional antibiotics, the bacteriophage of the present invention can kill the specific pathogens without affecting beneficial bacteria. Furthermore, the bacteriophage of the present invention does not induce drug resistance so that it can be provided as a novel antibiotic with a long life cycle.

In accordance with a further aspect thereof, the present invention pertains to an animal feed or drinking water, comprising the bacteriophage as an active ingredient.

Feed additive antibiotics used in the fishery and livestock industry are intended to prevent infections. However, most of the currently available feed additive antibiotics are problematic in that they are apt to induce the occurrence of resistant strains and may be transferred to humans as they remain in livestock products. The uptake of such residual antibiotics may make human pathogens resistant to antibiotics, resulting in the spread of diseases. Furthermore, many kinds of feed additive antibiotics, usually used in combination in animal feeds, may cause the emergence of multidrug-resistant strains. Therefore, the bacteriophage of the present invention can be used as a feed additive antibiotic that is eco-friendly enough to be a solution to the problems.

The animal feed according to the present invention may be prepared by adding the bacteriophage directly or in a separate feed additive form to an animal feed. In an animal feed, the bacteriophage of the present invention may take a liquid or a dry form, and preferably exist as a dried powder. In this regard, the bacteriophage of the present invention may be dried by air drying, natural drying, spray drying or freeze-drying, but these drying processes do not limit the present invention. The bacteriophage of the present invention may be added as powder in an amount of from 0.05 to 10% by weight, preferably in an amount of from 0.1 to 2% by weight, based on the total weight of animal feed. The animal feed may comprise other conventional additives useful for the preservation thereof for a long term, in addition to the bacteriophage of the present invention.

To the feed additive of the present invention may be added another non-pathogenic microorganism. The available additional microorganism may be selected from the group consisting of *Bacillus subtilis* that can produce protease, lipase and invertase, *Lactobacillus* sp. strain that can exert physiological activity and a function of decomposing under an aerobic conditions, such as in the stomach of cattle, filamentous fungi including *Aspergillus oryzae* (J Animal Sci 43:910-926, 1976) that increases the weight of domestic animals, enhances milk production and helps the digestion and absorptiveness of feeds, and yeast including *Saccharomyces cerevisiae* (J Anim Sci 56:735-739, 1983).

The animal feed comprising ΦCJ4 in accordance with the present invention may include plant-based feeds, such as grains, nuts, food byproducts, seaweed, fiber, drug byproducts, oil, starches, meal, and grain byproducts, and animal-based feeds such as proteins, minerals, fat, single cell proteins, zooplankton, and food wastes, but is not limited thereto.

The feed additive comprising φCJ4 in accordance with the present invention may include additives for preventing quality deterioration, such as binders, emulsifiers and preservatives, and additives for increasing utility, such as amino acids, vitamins, enzymes, probiotics, flavorings, non-protein nitrogen, silicates, buffering agents, coloring agents, extracts, and oligosaccharides, but is not limited thereto.

When supplied with drinking water containing the bacteriophage of the present invention, livestock can be continuously reduced in the population of *Salmonella* bacteria in the intestine thereof livestock. As a result, *Salmonella*-free livestock can be produced.

In accordance with still a further aspect thereof, the present invention pertains to a cleaner or a sanitizer, comprising the bacteriophage as an active ingredient.

The sanitizer comprising the bacteriophage as an active ingredient is very useful for food hygiene against, for example, food poisoning. In detail, the sanitizer may be utilized not only as an agent or a food additive for preventing *Salmonella* contamination, but also in the production of *Salmonella*-free livestock. In order to remove *Salmonella*, the sanitizer can also be sprayed over domestic sewages and applied to poultry barns, slaughterhouses, spots where livestock died, cooking spaces and cooking facilities.

Further, the cleaner comprising the bacteriophage as an active ingredient can be used on a body area of living animals, such as skin, feathers and the like, which is already or potentially contaminated with *Salmonella* bacteria.

In accordance with still another aspect, the present invention relates to a method for the prevention or treatment of infectious diseases caused by one or more *Salmonella* bacteria selected from the group consisting of *Salmonella enteritidis, Salmonella typhimurium, Salmonella gallinarum*, and *Salmonella pullorum* using the bacteriophage or the composition.

The composition of the present invention may be administered in the form of a pharmaceutical formulation into animals or may be ingested as a mixture with animal feed or drinking water by animals and preferably as a mixture with animal feed. In the present invention, the animals include cattle, pigs, chicken, poultry and humans, but are not limited thereto.

As long as it reaches target tissues, any route, whether oral or parenteral, may be taken for administering the composition of the present invention. In detail, the composition of the present invention may be administered via oral, rectal, topical, intravenous, intraperitoneal, intramuscular, intraarterial, transdermal, intranasal, and inhalation routes.

The method for the treatment of diseases in accordance with the present invention comprises administering the composition of the present invention in a therapeutically effective amount. It is apparent to those skilled in the art that the total daily dose should be determined by an attending physician or veterinarian within the scope of sound medical judgment. The therapeutically effective amount for a given patient may vary depending on various factors well known in the medical art, including the kind and degree of the response to be achieved, the patient's age, body weight, state of health, sex, and diet, time and route of administration, the secretion rate of the composition, the time period of therapy, concrete compositions according to whether other agents are used therewith or not, etc.

In accordance with still another aspect, the present invention relates to a method for preventing infectious diseases caused by *Salmonella enteritidis, Salmonella typhimurium, Salmonella gallinarum* or *Salmonella pullorum*, using the bacteriophage that has a specific bactericidal activity against *Salmonella enteritidis, Salmonella typhimurium, Salmonella gallinarum*, or *Salmonella pullorum*.

In a preferred embodiment, the present invention has found that the bacteriophage ΦCJ4 can be used to prevent horizontal transmission of SG in commercial layer chickens. In particular, six-week-old chickens, each challenged with $5 \times 10^8$ CFU of SG, cohabited with contact chickens treated with $10^6$ PFU/kg of bacteriophage, prepared in feed additives, for 7 days before, and 21 days after challenge with SG. Bacteriophage therapy using ΦCJ4 decreased the incidence of organ invasion and produced a significant ($P<0.05$) reduction in mortality in the contact chickens when compared to the untreated contact chickens (see Tables 9 and 10). Considering the fact that the horizontal transmission of *Salmonella* species usually occurs following ingestion of feces of clinically infected chickens or carriers (Jordan, F. T. W. and M. Pattison., Poultry disease., W.B. Saunders Company Ltd., London, U.K. 4: 169-171, 1992), these results suggest that the presence of ΦCJ4 in the intestinal tract of contact chickens might inhibit the SG growth that causes septicemia, as well as provide protection from the horizontal spread of SG due to reduced bacterial shedding and environmental contamination.

In general, the viability of an orally administered bacteriophage may be rapidly reduced under the acidic conditions of the stomach and in the presence of enzymes and other digestive compounds such as bile (Ma, Y. et al., Appl. Environ. Microbiol. 74: 4799-4805, 2008). Thus, a bacteriophage might not survive during gastric passage. However, in the present invention, sufficient ΦCJ4 was identified in feed during the experiment, and was isolated from organs and feces of chickens that received ΦCJ4 in the feed additive, to indicate that ΦCJ4 are stable in feed and did pass through the digestive tract, reach the infection site, and kill the SG. This scenario is plausible because the stomach pH is likely to be much higher after feeding due to the buffering effect of the ingested food (Zhu, H. et al., J. Med. Microbiol. 55: 1265-1270, 2006).

In many poultry industries, live and inactivated killed SG vaccines have been applied to prevent and control the incidence of the disease. Although SG vaccines can reduce clinical signs, they do not provide complete protection against bacterial shedding in SG-infected chickens (Lee, Y. J. et al., Avian Pathol. 36: 495-498, 2007). Therefore, the sole use of SG vaccine in poultry farms may allow chickens to shed bacteria although remaining symptomatically subclinical, which could encourage horizontal transmission and complicate SG eradication. The use of bacteriophage therapy in combination with vaccines or competitive exclusion has proven very successful in limiting *Salmonella* infections in chickens (Methner, U. et al., Int. J. Food Microbiol. 49: 35-42, 1999). Therefore, based on the above results, bacteriophage ΦCJ4 containing feed additives in combination with SG vaccine could be helpful in controlling SG in the poultry industry.

In conclusion, the present invention has demonstrated that bacteriophage treatment using ΦCJ4 could markedly curtailed the mortality and organ invasion in chickens exposed to virulent strains of SG via horizontal transmission. These results provide important insight into preventive and control strategies against *Salmonella* infection and suggest that use of ΦCJ4 may constitute a novel, safe, and effectively plausible alternative to antibiotics for the prevention of *Salmonella* infection in poultry.

Hereinafter, the present invention will be described in more detail with reference to the following Examples. However, these Exam pies are for illustrative purposes only, and the invention is not intended to be limited by these Examples.
[Mode For Invention]

EXAMPLE 1

*Salmonella* Bacteriophage Isolation 1-1. Bacteriophage Screening and Single Bacteriophage Isolation 50 ml of each sample from a chicken slaughterhouse, located in Suwon City, Kyeonggi Do, South Korea, and a nearby sewage disposal plant were transferred to a centrifuge tube, and centrifuged at 4000 rpm for 10 min, followed by filtering the supernatant through a 0.45 μm filter. 18 mL of the sample filtrate was mixed with 150 μl of a *Salmonella gallinarum* (hereinafter referred to as "SG") shaking culture medium ($OD_{600}=2$) and 2 ml of 10× Luria-Bertani medium (hereinafter referred to as "LB medium") tryptone 10 g; yeast extract 5 g; NaCl 10 g; in a final volume of 1 L). The mixture was cultured at 37□ for 18 hrs and then centrifuged at 4000 rpm for 10 min after which the supernatant was filtered through a 0.2 μm filter. Separately, a mixture of 3 ml of 0.7% agar (w/v) and 150 μl of the SG shaking culture medium ($OD_{600}=2$) was poured across an LB plate and allowed to solidify. Over this plate was spread 10 μl of the culture filtrate, followed by incubation for 18 hrs at 37° C. (0.7% agar was used as "top-agar" and the titration of phage lysate was performed on the top-agar, called soft agar overlay technique).

A dilution of the sample culture medium containing the phage lysate was mixed with 150 μL of an SG shaking culture medium ($OD_{600}=2$) and subjected to soft agar overlay assay to produce single plaques. Since a single plaque consisted of the same bacteriophage, one plaque was taken and dissolved in 400 μL of an SM solution (NaCl, 5.8 g; $MgSO_4 7H_2$ 0.2 g; 1M Tris-Cl (pH7.5), 50 ml; $H_2O$, in a final volume of 1 L), and left for 4 hours at room temperature to isolate single bacteriophages. To amplify the isolated bacteriophage, 100 μL of the supernatant was taken from the single bacteriophage solution, mixed with 12 mL of 0.7% agar and 500 μL of an SG shaking culture medium, and subjected to a soft agar overlay assay on an LB plate (150 mm in diameter). 15 mL of an SM solution was poured to a plate in which lysis had been completed, after which the plate was gently shaken for 4 hrs at room temperature to elute the bacteriophages from the top-agar. The SM solution containing the eluted bacteriophages was recovered, and chloroform was added in an amount corresponding to 1% of the final volume, and mixed well for 10 min. After centrifugation at 4000 rpm for 10 minutes, the resulting supernatant was filtered through a 0.2 μm filter, and stored in the refrigerator until use.

1-2. Large-Scale Batches of Bacteriophage

The selected bacteriophage was cultured at a large scale using SG. SG was cultured with shaking. After an aliquot of $1.5 \times 10^{10}$ cfu (colony forming units) was centrifuged at 4000 rpm for 10 min, the pellet was re-suspended in 4 ml of an SM solution. Into the suspension was inoculated $7.5 \times 10^7$ pfu (plaque forming unit) of the bacteriophage at an MOI (multiplicity of infection) of 0.005), followed by incubation at 37° C. for 20 min. This solution was inoculated into 150 mL of an LB media in a flask, and cultured at 37° C. for 5 hrs. Chloroform was added in an amount corresponding to 1% of the final volume before the culture solution was shaken for 20 min. DNase I and RNase A were added to a final concentration of 1 μg/ml, each. The solution was left at 37° C. for 30 min. NaCl and PEG (polyethylene glycol) were added to a final concentration of 1 M and 10% (w/v), respectively and left at 4° C. for an additional 3 hrs. The solution was centrifuged at 4° C. and 12,000 rpm for 20 min to discard the supernatant. A suspension of the pellet in 5 mL of an SM solution was left at room temperature for 20 minutes and mixed well with 4 mL of chloroform. After centrifugation at 4° C. and 4000 rpm for 20 min, the supernatant was filtered through a 0.2 μm filter and then subjected to ultracentrifugation using a glycerol density gradient to purify ΦCJ4 (density: 40%, 5% glycerol at 35,000 rpm and 4° C. for 1 hr). The purified ΦCJ4 was re-suspended in 300 μL of an SM solution, followed by titration. ΦCJ4 was deposited with the Korean Culture Center of Microorganisms (361-221, Honje 1, Seodaemun, Seoul) on Aug. 14, 2009 under accession number KCCM11027P.

EXAMPLE 2

Examination on ΦCJ4 Infection of *Salmonella*

To analyze the selected bacteriophage for lytic activity on *Salmonella* species other than SG, attempts were made of cross infection with other *Salmonella* species. As a result, ΦCJ4 did not infect SC (*Salmonella enterica* Serotype Choleraesuis), SD (*Salmonella enterica* Serotype Derby), SA (*Salmonella enterica* sub sp. *Arizonae*), and SB (*Salmonella enterica* sub sp. *Bongori*), but infected SE (*Salmonella enteritidis*), ST (*Salmonella typhimurium*), SG (*Salmonella gallinarum*) and SP (*Salmonella pullorum*)(see Example 12). The results are summarized in Table 1, below and shown in FIG. 1.

TABLE 1

ΦCJ4 Infection of *Salmonella*

| Sero type | Strain name | Plaque formation | Sero type | Strain name | Plaque formation |
|---|---|---|---|---|---|
| SE | SGSC 2282 | ○ | SA | ATCC 13314 | X |
| ST | ATCC 14028 | ○ | SB | ATCC 43975 | X |
| SG | SGSC 2293 | ○ | SC | ATCC 10708 | X |
| SP | SGSC 2295 | ○ | SD | ATCC 6960 | X |

ATCC: The Global *BioresourceCenter*
SGSC: *Salmonella* Genetic Stock Center

EXAMPLE 3

Morphology of Bacteriophage ΦCJ4

The purified ΦCJ4 was diluted in a 0.01% gelatin solution, and then fixed in a 2.5% glutaraldehyde solution. The sample was dropped onto a carbon-coated mica plate (ca.2.5×2.5 mm), adapted for 10 min, and washed with sterile distilled water. A carbon film was mounted on a copper grid, stained with 4% uranyl acetate for 30-60 sec, and dried. Examination under a JEM-1011 transmission electron microscope (at 80 kV, magnification of ×120,000-×200,000) had it that the purified ΦCJ4 consisted morphologically of an isometric capsid and a long non-contractile tail, indicating that it belongs to a morphotype group of the family Siphoviridae.

EXAMPLE 4

Protein Pattern Analysis of ΦCJ4

15 μL of a ΦCJ4 solution purified at a titer of $10^{11}$ pfu/ml was mixed with 3 μL of a 5×SDS sample solution, and heated for 5 min. The total protein of ΦCJ4 was run on 4-12% NuPAGE Bis-Tris gel (Invitrogen). Then, the gel was stained with Coomassie blue for 1 hr at room temperature. Major bands were detected at 40 kDa and 17 kDa with the appearance of other bands at 69 kDa, 38 kDa and 14 kDa, as shown in FIG. 3.

EXAMPLE 5

Total Genomic DNA Size of ΦCJ4

Genomic DNA of ΦCJ4 was isolated using ultracentrifugation. In this regard, to a purified ΦCJ4 culture medium were added EDTA (ethylenediaminetetraacetic acid (pH8.0)), proteinase K, and SDS (sodium dodecyl sulfate) at a final concentration of 20 mM, 50 ug/ml, and 0.5% (w/v), respectively, followed by incubation at 50° C. for 1 hr. An equal volume of phenol (pH 8.0) was added and mixed well. After centrifugation at 12,000 rpm and room temperature for 10 min, the supernatant was mixed well with an equal volume of PCI (phenol:chloroformisoamylalhocol=25:24:1). Another centrifugation at 12,000 rpm and room temperature for 10 min produced a supernatant which was then mixed with 1/10 volume of 3 M sodium acetate and two volumes of cold 95% ethanol, and left at −20° C. for 1 hr. After centrifugation at 0° C. and 12,000 rpm for 10 min, the supernatant was completely removed, and the DNA pellet was dissolved in 50 μL of TE (Tris-EDTA, pH 8.0). The extracted DNA was diluted 10-fold, and measured for absorbance at $OD_{260}$ to determine its concentration 1 μg of the total genomic DNA was loaded onto 1% PFGE (pulse-field gel electrophoresis) agarose gel and electrophoresed at room temperature for 20 hrs with the aid of a BIO RAD PFGE system program 7 (size range 25-100 kbp; switch time ramp 0.4-2.0 seconds, linear shape; forward voltage 180 V; reverse voltage 120 V). As shown in FIG. 4, the genomic DNA of ΦCJ4 was approximately 42 kb long.

EXAMPLE 6

Genetic Analysis of ΦCJ4

The genetic analysis of the purified ΦCJ4 started with triple digesting 1 μg of the genomic DNA of ΦCJ4 with the restriction enzymes, EcoR V, Sca I and Nru I. Separately, another triple digestion was performed with the restriction enzymes StuI, PvuII, and HincII. The vector pCL1920 (Promega) was digested with Sma I, and treated with CIP (calf intestinal alkaline phosphatase). The digested genomic DNA was mixed at a ratio of 3:1 with the vector, and ligated at 16° C. for 5 hrs. The resulting recombinant vector was transformed into *E. coli* DH5α which was then plated on an LB plate containing kanamycin and X-gal (5-bromo-4-chloro-3-indolyl-beta-D-galactopyranoside) for blue/white selection. The selected colonies were cultured for 16 hrs in a culture medium containing kanamycin with shaking. Then, plasmids were extracted using a plasmid purification kit (Promega).

The cloning of the plasmids was confirmed by PCR using a primer set of FRT135 and FRT136 (SEQ ID NOS. 19 and 20, respectively), and selection was made only of insert fragments having a size of 1 kb or longer. Their base sequences were analyzed using the primer set of FRT135 and FRT136 (SEQ ID NOS. 19 and 20, respectively). The base sequences thus obtained were given in SEQ ID NOS. 1 to 6, respectively, and analyzed for sequence similarity with the aid of a NCBI blast (program, and the results are summarized in Table 2, below.

TABLE 2

Sequence Similarity between ΦCJ4 and Other Bacteriophages

| No | Organism | Protein | Accession number | Subject location | Query location | Identity | E value |
|---|---|---|---|---|---|---|---|
| 1 | *Salmonella* phage KS7 | hypothetical protein BPKS7gp56 | YP_308656 | 187-528 | 3-1022 | 286/347 (82%) | 6e−124 |
| 2 | *Salmonella* phage KS7 | hypothetical protein BPKS7gp41 | YP_224063.1 | 1-212 | 80-715 | 202/212 (95%) | 1e−94 |
|  | *Salmonella* phage SETP3 | DNA polymerase | YP_001110810 | 1-212 | 80-715 | 198/212 (93%) | 4e−91 |
| 3 | *Salmonella* phage KS7 | hypothetical protein BPKS7gp56 | YP_308656 | 187-479 | 3-881 | 274/293 (93%) | 3e−139 |

TABLE 2-continued

Sequence Similarity between ΦCJ4 and Other Bacteriophages

| No | Organism | Protein | Accession number | Subject location | Query location | Identity | E value |
|---|---|---|---|---|---|---|---|
| 4 | *Salmonella* phage KS7 | hypothetical protein BPKS7gp50 | YP_224072 | 1-180 | 540-1 | 172/180 (95%) | 5e−95 |
| | *Salmonella* phage SETP3 | tailspike protein | YP_001110804 | 1-180 | 540-1 | 171/180 (95%) | 3e−94 |
| | *Salmonella* phage SETP3 | tail component protein | YP_001110803 | 467-598 | 951-556 | 124/132 (93%) | 1e−66 |
| | *Salmonella* phage KS7 | hypothetical protein BPKS7gp51 | YP_224073 | 578-709 | 951-556 | 122/132 (92%) | 3e−65 |
| 5 | *Salmonella* phage KS7 | hypothetical protein BPKS7gp57 | YP_308657 | 1-96 | 567-854 | 95/96 (98%) | 8e−56 |
| | *Salmonella* phage KS7 | hypothetical protein BPKS7gp58 | YP_308658 | 1-78 | 196-429 | 77/78 (98%) | 1e−13 |
| 6 | *Salmonella* phage SETP3 | tail component protein | YP_001110803 | 201-531 | 1-993 | 324/331 (97%) | 6e−124 |
| | *Salmonella* phage KS7 | hypothetical protein BPKS7gp51 | YP_224073 | 312-642 | 1-993 | 322/331 (97%) | 1e−123 |

EXAMPLE 7

Design of ΦCJ4-Specific Primer Sequences

In order to identify ΦCJ4, ΦCJ4-specific primers were designed on the basis of SEQ ID NOS. 1 to 6. PCR was performed using each primer set of SEQ ID NOS. 7 and 8, SEQ ID NOS. 9 and 10, SEQ ID NOS. 11 and 12, SEQ ID NOS. 13 and 14, SEQ ID NOS. 15 and 16 and SEQ ID NOS. 17 and 18. 0.1 μg of the genomic DNA of bacteriophage and 0.5 pmol of each primer were added to pre-mix (Bioneer), and the final volume was adjusted to 20 μL. PCR was performed with 30 cycles of denaturation; 94° C. for 30 sec, annealing; 60° C. for 30 sec, and polymerization; 72° C. for 1 min. The PCR products thus obtained were approximately 860 bp, 600 bp, 900 bp, 950 bp, 700 bp, and 880 bp long, respectively, with the primer sets of SEQ ID NOS. 7 and 8, SEQ ID NOS. 9 and 10, SEQ ID NOS. 11 and 12, SEQ ID NOS. 13 and 14, SEQ ID NOS. 15 and 16 and SEQ ID NOS. 17 and 18. The results are shown in FIG. 5.

EXAMPLE 8 pH Stability of Bacteriophage

Figure 6:
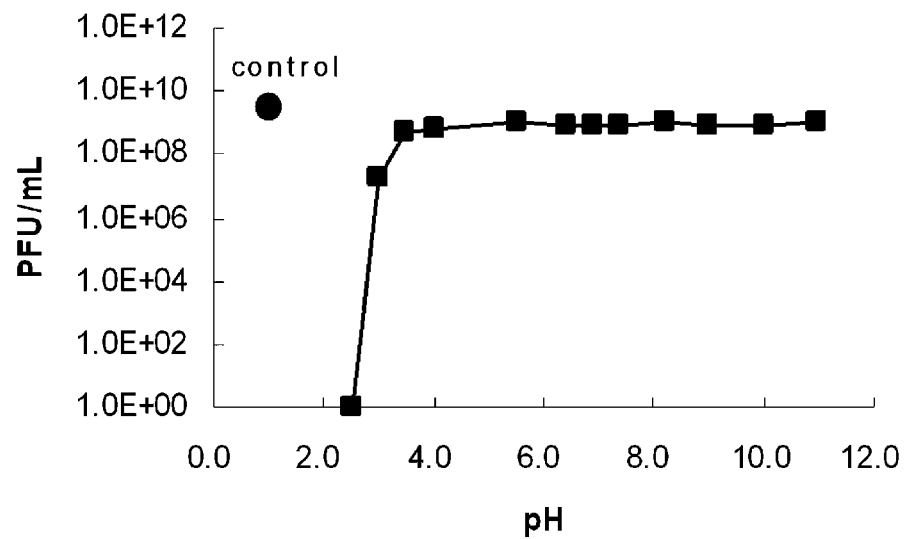
FIG. 6 is the result of acid-resistance assay on the bacteriophage ΦCJ4, showing the number of surviving bacteriophage at pH 2.5, 3.0, 3.5, 4.0, 5.5, 6.4, 6.9, 7.4, 8.0, 9.0, 10.0 and 11.0. The bacteriophage ΦCJ4 did not lose its activity until pH 3.0, but completely lost its activity at pH 2.5 or lower, as compared to control.

In order to determine whether ΦCJ4 survives the low pH environment in the stomach of livestock, ΦCJ4 was assayed for stability in a wide range of pH (pH 2.5, 3.0, 3.5, 4.0, 5.5, 6.4, 6.9, 7.4, 8.2, 9.0, 10.0, 11.0). Various pH solutions [sodium acetate buffer (pH 4.0, pH 5.5, pH 6.4), sodium citrate buffer (pH 2.5, pH 3.0, pH 3.5), sodium phosphate buffer (pH 6.9, pH 7.4) and Tris-HCl (pH 8.2, pH 9.0, pH 10.0, pH 11.0)] were prepared to have a concentration of 2 M. 180 μL of each pH solution was mixed with 20 μL of a bacteriophage solution ($1.0 \times 10^{10}$ pfu/ml), followed by incubation at room temperature for 2 hr. The reaction solution was serially diluted, and 10 μL of each dilution was cultured at 37° C. for 18 hrs by a soft agar overlay method to determine the titers of the phage lysates. Titer changes with pH were measured to determine the stability of bactriophage over pH in comparison to titers of ΦCJ4 at 0 hr. The results showed that the bacteriophage did not lose its activity and remained stable down to pH 3.5. The results are shown in FIG. 6.

EXAMPLE 9

Heat Stability of Bacteriophage

For use as a feed additive, the bacteriophage was assayed for stability to the heat generated during a formulation process. In this regard, 200 μL of a ΦCJ4 solution with a titer of $1.0 \times 10^{10}$ pfu/ml was incubated at 37° C., 45° C., 53° C., 60° C.; 70° C., or 80° C. for 2 hr. The solution was serially diluted, and 10 μL of each dilution was cultured at 37° C. for 18 hrs by a soft agar overlay method to determine the titers of phage lysates. Titer changes with temperature and exposure time were measured to determine the stability of bacteriophage to heat in comparison to titers at 0 hr and 37° C. The results showed that the bacteriophage did not lose its activity at 70° C. for up to 2 hrs, but was deactivated at 80° C. or higher. The results are shown in FIG. 7.

EXAMPLE 10

Desiccation Tolerance of Bacteriophage

For use as a feed additive, the bacteriophage was assayed for tolerance to the dry condition set for a formulation process. On the basis of the results obtained from the heat stability assay, an assay was performed at 60° C. for 2 hr as follows. 200 μL of a ΦCJ4 solution ($1.0 \times 10^{11}$ pfu/ml) was dried using a Speed vacuum (Speed-Vacuum Concentrator 5301, Eppendorf). The pellet thus obtained was completely re-suspended overnight at 4° C. in an equal volume of an SM solution. The solution was serially diluted, and 10 μL of each dilution was cultured at 37° C. for 18 hrs using a soft agar overlay method to determine the titers of phage lysates. Titer changes under the dry condition were measured to determine the desiccation tolerance of the bacteriophage in comparison with pre-drying titers. The results showed that its activity was decreased about 10-fold. The results are shown in FIG. 8.

EXAMPLE 11

Spectrum of Wild-Type Host Cell Strains to which Bacteriophage Infects

ΦCJ4 was assayed for lytic activity against Korean wild-type SE (38 strains), ST (22 strains), SG (56 strains) and SP (19 strains), obtained from Laboratory of Avian Diseases, College of Veterinary Medicine, Seoul National University, and National Veterinary Research and Quarantine Service and the Korea Centers for Disease Control and Prevention, in addition to the strains used in the present invention, SE (SE SCSG 2282), ST (ST ATCC 14028), SG (SG SGSC2293) and SP(SP SGSC2295). 150 µL of each strain shaking culture medium (OD$_{600}$=2) was mixed, and 10 µL of ΦCJ4 solution ($10^{10}$ pfu/ml) was cultured at 37° C. for 18 hrs using a soft agar overlay method to monitor the formation of plaques. It was observed that the bacteriophage ΦCJ4 showed lytic activity of 97% against SE, 91% against ST, 96% against SG and 85% against SP. The results are summarized in Table 3, below.

TABLE 3

Lytic Activity of ΦCJ4 against Korean Wild-Type Strains SE, ST, SG, and SP

| Sero type | Strain name | Plaque formation | Sero type | Strain name | Plaque formation |
|---|---|---|---|---|---|
| SG | SNU SG1 | ○ | ST | SNU ST1 | ○ |
| | SNU SG2 | ○ | | SNU ST2 | ○ |
| | SNU SG3 | ○ | | SNU ST3 | ○ |
| | SNU SG4 | ○ | | SNU ST4 | ○ |
| | SNU SG5 | ○ | | SNU ST7 | ○ |
| | SNU SG6 | ○ | | SNU ST8 | ○ |
| | SNU SG7 | ○ | | SNU ST11 | ○ |
| | SNU SG8 | ○ | | SNU ST12 | ○ |
| | SNU SG9 | ○ | | SNU ST13 | ○ |
| | SNU SG10 | ○ | | SNU ST14 | ○ |
| | SNU SG11 | ○ | | SNU ST17 | ○ |
| | SNU SG12 | ○ | | SNU ST18 | X |
| | SNU SG13 | ○ | | SNU ST19 | X |
| | SNU SG14 | ○ | | SNU ST20 | ○ |
| | SNU SG15 | ○ | | SNU ST25 | ○ |
| | SNU SG16 | ○ | | SNU ST26 | ○ |
| | SNU SG17 | ○ | | SNU ST37 | ○ |
| | SNU SG18 | ○ | | SNU ST38 | ○ |
| | SNU SG19 | ○ | | SNU ST41 | ○ |
| | SNU SG20 | ○ | | SNU ST42 | ○ |
| | SNU SG21 | ○ | | ATCC UK1 | ○ |
| | SNU SG22 | ○ | | ATCC 14028S | ○ |
| | SNU SG23 | ○ | | SGSC STM1412 | ○ |
| | SNU SG24 | ○ | | SGSC STM260 | ○ |
| | SNU SG25 | ○ | | SGSC STM SA2197 | ○ |
| | SNU SG26 | ○ | SE | SGSC SE2282 | ○ |
| | SNU SG27 | ○ | | SGSC SE2377 | ○ |
| | SNU SG28 | ○ | | PT4 S1400194 | ○ |
| | SNU SG30 | ○ | | PT4 LA52 | ○ |
| | SNU SG31 | ○ | | NVRQS SE004 | ○ |
| | SNU SG32 | ○ | | NVRQS SE005 | ○ |
| | SNU SG33 | ○ | | KCDC SE008 | ○ |
| | SNU SG34 | ○ | | KCDC SE009 | ○ |
| | SNU SG36 | ○ | | KCDC SE010 | ○ |
| | SNU SG37 | ○ | | KCDC SE011 | X |
| | SNU SG38 | ○ | | KCDC SE012 | ○ |
| | SNU SG39 | ○ | | KCDC SE013 | ○ |
| | SNU SG40 | ○ | | KCDC SE014 | ○ |
| | SNU SG41 | ○ | | KCDC SE015 | ○ |
| | SNU SG42 | ○ | | KCDC SE016 | ○ |
| | SNU SG43 | ○ | | KCDC SE017 | ○ |
| | SNU SG44 | ○ | | KCDC SE018 | ○ |
| | SNU SG45 | ○ | | KCDC SE019 | ○ |
| | SNU SG46 | ○ | | KCDC SE020 | ○ |
| | SNU SG47 | ○ | | KCDC SE021 | ○ |
| | SNU SG48 | ○ | | KCDC SE022 | ○ |
| | SNU SG49 | ○ | | KCDC SE023 | ○ |
| | SNU SG50 | ○ | | KCDC SE024 | ○ |
| | SGSC SG9184 | ○ | | KCDC SE025 | ○ |
| | SGSC SG2292 | ○ | | KCDC SE026 | ○ |
| | SGSC SG2293 | ○ | | KCDC SE027 | ○ |
| | SGSC SG2744 | ○ | | KCDC SE028 | ○ |
| | SGSC SG2796 | ○ | | KCDC SE029 | ○ |
| SP | SNU SP1 | ○ | | KCDC SE030 | ○ |
| | SNU SP4 | ○ | | KCDC SE031 | ○ |
| | SNU SP5 | ○ | | KCDC SE032 | ○ |
| | SNU SP8 | ○ | | KCDC SE033 | ○ |
| | SNU SP11 | ○ | | KCDC SE034 | ○ |
| | SGSC SP2294 | ○ | | KCDC SE035 | ○ |
| | SGSC SP2295 | ○ | | KCDC SE036 | ○ |
| | SGSC SP2737 | X | | KCDC SE037 | ○ |
| | SGSC SP2739 | X | SC | ATCC SC10708 | X |
| | SGSC SP2742 | ○ | | ATCC SC2929 | X |
| | SGSC SP2743 | ○ | SD | ATCC SD6960 | X |
| | SGSC SP2745 | ○ | | ATCC SD2466 | ○ |
| | SGSC SP2751 | ○ | | ATCC SD2467 | ○ |
| | SGSC SP4663 | X | | ATCC SD2468 | X |
| | SGSC SP4664 | ○ | SA | ATCC SA13314 | X |
| | SGSC SP4665 | ○ | SB | ATCC SB43975 | X |
| | SGSC SP4666 | ○ | | | |
| | SGSC SP4667 | ○ | | | |
| | SGSC SA1684 | ○ | | | |

SNU: Laboratory of Avian Diseases, College of Veterinary Medicine, Seoul National University
SGSC: *Salmonella* genetic stock center
NVRQS: National Veterinary Research & Quarantine Service
KCDC: Korean Centers for Disease Control and prevention
ATCC: The Global Bioresource Center, American Type Culture Collection

EXAMPLE 12

Toxicity Assay of Bacteriophage

Figure 9:
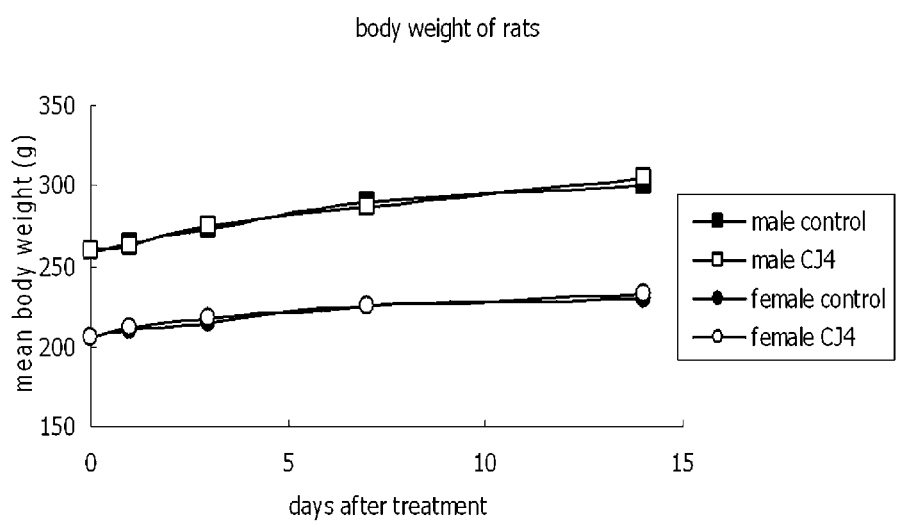
FIG. 9 is a graph in which body weights of rats are plotted against time after administration with single dosages of the bacteriophage ΦCJ4. ■; male control administered with 20 mM Tris-HCl and 2 mM $MgCl_2$ mix, □; male control administered at a concentration of $1 \times 10^{12}$ pfu with ΦCJ4, ●; female control administered with 20 mM Tris-HCl and 2 mM $MgCl_2$ mix, ○; female test group administered at a concentration of $1 \times 10^{12}$ pfu with ΦCJ4. No significant changes in body weight were found even 14 days after the administration, in comparison with the control.

For safety use in the prevention of salmonellosis, *Salmonella* food poisoning, fowl typhoid and *pullorum*, the bacteriophage was in vivo assayed for toxicity. Toxicity assay was performed with single oral dosages. In this assay, rats were orally administered with a single dosage of ΦCJ4 and monitored for acute toxicity to determine approximate lethal concentrations of ΦCJ4. To this end, first, specific-pathogen free (SPF) male and female rats (SD) 7 weeks old, each of 10, were starved for 24 hrs before administration with ΦCJ4. On the administration day, five males and five females were orally administered at a dose of 10 mL/kg with ΦCJ4 having a titer of $1 \times 10^{12}$ pfu/ml using an oral sonde while five controls were orally administered with a 20 mM Tris-HCl and 2 mM MgCl$_2$ mix. Four hrs after the oral administration, feeds were provided for rats. Monitoring was conducted every hour for 4 hours, starting from 30 min after the administration on the day of administration. Since then, they were monitored once a day for 14 days for general symptoms. None of them died. Neither toxic symptoms nor noticeable clinical symptoms were generated by ΦCJ4. The results are summarized in Tables 4 and 5, below. Body weights were recorded before and 1 3, 7, 10 and 14 days after administration. No significant changes were observed in body weight, indicating that ΦCJ4 does not cause a toxic reaction sufficient to reduce appetite or to change the body weight. These results are shown in FIG. 9. No noticeable abnormalities were found in any organ as examined by autopsy and with the naked eye. Therefore, the novel bacteriophage ΦCJ4 is non-toxic.

TABLE 4

Oral Toxicity Assay of ΦCJ4 in Terms of Mortality

| | Done | Hours after treatment | | | | Days after treatment | | | | | | | | | | Final |
|---|---|---|---|---|---|---|---|---|---|---|---|---|---|---|---|---|
| Sex | (Pfu/kg) | 0.5 | 1 | 2 | 3 | 4 | 5 | 6 | 7 | 8 | 9 | 10 | 11 | 12 | 13 | 14 | Mortality |
| Male | Control | 0 | 0 | 0 | 0 | 0 | 0 | 0 | 0 | 0 | 0 | 0 | 0 | 0 | 0 | 0 | 0/5 |
|  | $10^{13}$ | 0 | 0 | 0 | 0 | 0 | 0 | 0 | 0 | 0 | 0 | 0 | 0 | 0 | 0 | 0 | 0/5 |
| Female | control | 0 | 0 | 0 | 0 | 0 | 0 | 0 | 0 | 0 | 0 | 0 | 0 | 0 | 0 | 0 | 0/5 |
|  | $10^{13}$ | 0 | 0 | 0 | 0 | 0 | 0 | 0 | 0 | 0 | 0 | 0 | 0 | 0 | 0 | 0 | 0/5 |

TABLE 5

Oral Toxicity Assay of ΦCJ4 in Terms of General Symptoms

| | Done | Final Mortality | | Clinical Signs | |
|---|---|---|---|---|---|
| Sex | Pfu/kg | Male | Female | Male | Female |
| Male | Control | 0/5 | 0/5 | 0/5 | 0/5 |
|  | $10^{13}$ | 0/5 | 0/5 | 0/5 | 0/5 |
| Female | Control | 0/5 | 0/5 | 0/5 | 0/5 |
|  | $10^{13}$ | 0/5 | 0/5 | 0/5 | 0/5 |

TABLE 6

Oral Toxicity Assay of ΦCJ4 in Terms of Organ Abnormality

| Sex | Done (pfu/kg) | Gross finding | Frequency |
|---|---|---|---|
| Male | Control | N.A.D | 5/5 |
|  | $10^{13}$ | N.A.D | 5/5 |
| Female | Control | N.A.D | 5/5 |
|  | $10^{13}$ | N.A.D | 5/5 | a: not detected.

EXAMPLE 13

Efficiency of Bacteriophage as a Cleaner

In order to evaluate the efficiency of the bacteriophage as a cleaner for meat products, the bacteriophage was assayed for ability to control *Salmonella* bacteria in comparison with a conventional cleaner. In this regard, 50 g of chicken breast cuts was purchased from a store. An ST shaking culture (O.D.=2) was adjusted to a concentration of $10^8$ cfu/ml and uniformly spread in an amount of 200 μL over the chicken breast cuts which were then dried at room temperature for 12 min. The bacteriophage ΦCJ4 and the cleaner chlorine (4-6% Sodium hypochlorite) were contained at a concentration of $10^8$ pfu/L and 50 ppm in respective sprayers and sprayed at a rate of one stroke/sec for 10 sec. The treated chicken breast cuts were placed in respective sanitary packs to which an SM buffer was then added. The packs were shaken in a semicircle pattern. The WCR (whole carcass rinse) thus obtained was serially diluted and the dilutions were spread over LB media, followed by incubation at 37° C. for 18 hrs to determine the number of ST. When treated with the bacteriophage ΦCJ4, the population of ST was 24.29% reduced. In contrast, the cleaner was observed to induce *Salmonella* bacteria to increase 14%. Accordingly, the bacteriophage ΦCJ4 has cleaning activity far better than that of the conventional cleaner. The results are given in Table 7, below.

TABLE 7

Comparison of Cleaning Efficiency between ΦCJ4 and Cleaner

| | Substance | Reduction Rate of *Salmonella* (%) |
|---|---|---|
| 1 | SM buffer | |
| 2 | Chlorine 50 ppm | (+14.50) |
| 3 | ΦCJ4 2.0 × $10^8$ pfu/L | 24.49 |

EXAMPLE 14

Prophylactic Efficacy Test on Bacteriophage

In order to evaluate the efficacy of ΦCJ4 on the prevention of SG, the following efficacy test was performed in chickens.

Six-week-old commercial layer chickens were obtained from a *Salmonella*-free chicken flock and were housed in a cage under strict biosecurity. The chickens were negative for antibodies against *Salmonella Enteritidis* and *Salmonella Typhimurium* by enzyme linked-immunosorbent assay (Biocheck, Foster City, Calif.) and against SG by a rapid serum agglutination (RSA) test. All experiments were carried out according to protocols approved by the Institutional Animal Care and Use Committee of the Konkuk University, Seoul, Korea.

*Salmonella Gallinarum* 2293 (SG2293), purchased from *Salmonella* Genetic Stock Center (Calgary, AB, Canada), was used and was designated as SG. Inocula for challenge were prepared from 18-24 hr Luria-Bertani (LB) broth cultures maintained at 37° C. After overnight incubation, the broth was centrifuged at 2500×g for 10 min and the bacterial pellet was suspended and serially diluted in sterile phosphate-buffered saline (pH 7.2). Bacterial enumeration of the suspension was performed using LB agar. The SG challenge strain is virulent for chickens and the 50% lethal dose of SG challenge strain, in challenged and contact chickens, was determined to be 5×$10^6$ CFU/ml and 5×$10^8$ CFU/ml, respectively.

Six-week-old commercial layer chickens (n=175) were divided into three experimental groups (Table 8).

TABLE 8

Experimental design

| Group | Number of chickens | Treatment |
|---|---|---|
| 1 SG challenged | 35 | SG challenged[A] with ΦCJ4 treatment[B] |
| SG free[C] | 35 | Only ΦCJ4 treated (SG free) |
| 2 SG challenged | 35 | Only SG challenged (ΦCJ4 free) |
| SG free[C] | 35 | Free of both SG and ΦCJ4 |

TABLE 8-continued

Experimental design

| Group | Number of chickens | Treatment |
|---|---|---|
| 3 Negative control[D] | 35 | Free of both SG and ΦCJ4 |

[A]Six-week-old chickens were orally challenged with SG (LP-93 strain) at a concentration of $5 \times 10^8$ CFU/bird.
[B]Chickens were treated with ΦCJ4 as a feed additive at a concentration of $10^6$ PFU/kg.
[C]Chickens were housed in the same cage with SG challenged chickens.
[D]Chickens in negative control were isolated from other groups.

Group 1 contained 70 birds; 35 birds were each orally-challenged with $5\times10^8$ CFUs of SG, then all the 70 birds were treated with $10^6$ PFU/kg of ΦCJ4, contained in the poultry feed, for 7 days before and 21 days after the SG challenge. Group 2 contained 70 birds; 35 birds were orally challenged with SG and 35 contact birds did not receive any treatment. In order to investigate horizontal transmission, stool samples from SG challenged and SG free birds were collected from the chickens of each Group and the presence of SG therein was detected. Group 3 contained 35 birds that were free of both SG and ΦCJ4 and was served as an unchallenged and untreated negative control. The chickens of Group 3 were raised separately without contact with the other groups.

To avoid a high density of chickens in any cage, which could change the dynamics of the spread of *Salmonella*, 70 chickens of groups 1 and 2 were divided into 4 cages, respectively. Forty chickens were housed in two cages (Cage 1=10 challenged chickens+10 contact chickens [n=20]; Cage 2=10 challenged chickens+10 contact chickens [n=20]) to observe mortality caused by SG horizontal transmission. Thirty chickens were housed in two cages (Cage 3=7 challenged chickens+8 contact chickens [n=15]; Cage 4=8 challenged chickens+7 contact chickens [n=15]) to observe the re-isolation rate of SG. The birds were monitored for mortality daily for 21 days after challenge. Sera samples were collected for SG antibody detection using RSA at 2 wk after challenge. At 7, 14, and 21 days postchallenge (dpc), the liver, spleen, and cecum were aseptically collected from 10 chickens per group (five challenged and five contact chickens) to re-isolate the SG challenge strain.

Bacteriologic analysis was performed as follows: An approximately 1 g tissue sample was macerated in 10 ml of buffered peptone water broth (Difco, Detroit, Mich.) and incubated overnight at 37° C. A 0.1-ml volume of culture was inoculated into Rappaport-Vassiliadis broth (Difco) and incubated at 37° C. for 48 hr prior to plating on xylose-lysine desoxycholate (Difco) and brilliant green agar (Difco). Plates were incubated at 37° C. for 24 hr and examined for the presence of SG. The identity of the challenge strain was confirmed using *Salmonella* antiserum (Difco).

Serologic tests were carried out as follows: SG antibodies were detected by the RSA plate test used as an authorized method in Korea[Choi Y.-J. et al. Korean J. Vet Serv. 23(4): 349-360, 2000]. The serum plate agglutination antigen was prepared with a homologous SG strain as described previously (Gast, R. K., Poult. Sci. 76: 17-23. 1997). For the reaction, 30 ml of antigen was mixed with an equal volume of serum on a clean, white tile marked into squares of about 3×3 cm². The mixture was observed for agglutination after 2 min of constant rotation. A positive reaction was indicated by easily visible clumping of the antigen within 2 min.

Statistical analysis was performed as follows: Mortality rate in chickens and SG re-isolation rate in organs were analyzed using a one-tailed Fisher's exact test. A P-value<0.05 was considered to be statistically significant.

In the serologic test, all the chickens were determined to be *Salmonella* seronegative prior to challenge and were demonstrated to be efficiently seroconverted to SG at 2 weeks after bacterial challenge, suggesting that horizontal transmission of SG had occurred (Table 9).

TABLE 9

Effect of ΦCJ4 on mortality caused by horizontal transmission of SG in commercial layers

| Group | Number of chickens | Antibodies against SG[A] Pre-challenge | Post-challenge | Mortality[B] (%) |
|---|---|---|---|---|
| *Phage-treated* | | | | |
| SG challenged | 20 | 0/15 | 15/15 | 10/20 (50) |
| SG free | 20 | 0/15 | 15/15 | 1/20 (5)* |
| *Untreated* | | | | |
| SG challenged | 20 | 0/15 | 15/15 | 11/20 (55) |
| SG free | 20 | 0/15 | 15/15 | 7/20 (35) |
| Negative control | 20 | 0/15 | 0/15 | 0/20 (0) |

Figure 10:
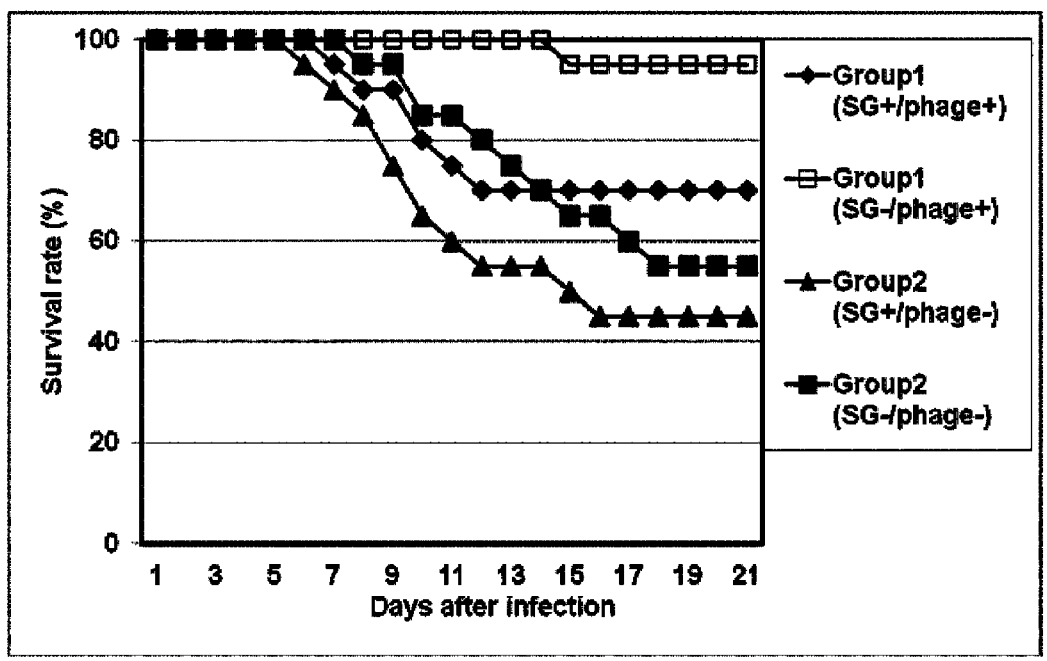
FIG. 10 is the results of comparing efficacy of ΦCJ4 on survival rate of SG challenged and contact chickens. Six-week-old chickens, each challenged with $5 \times 10^8$ CFUs of SG, cohabited with contact chickens treated with $10^6$ PFU/kg of ΦCJ4 prepared in feed additives for 7 days before, and 21 days after challenge with SG. Mortality was observed for 3 week after challenge. Asterisk (*) indicates significant difference (P<0.05) between ΦCJ4-treated and untreated contact chickens.

[A]RSA tests were performed for SG antibody detection at 2 weeks after challenge; number of chickens positive/number of chickens tested.
[B]Mortality was observed for 3 weeks after challenge; number of chickens positive/number of chickens tested.
*P < 0.05 by Fisher's exact test' as compared to untreated contact chickens Mortality of challenged chickens was first observed at 7 dpc (FIG. 10). Mortality rates of challenged and contact chickens that did not received with ΦCJ4 were 55% and 35%, but challenged and contact chickens treated with ΦCJ4 were 50% and 5%, respectively (Table 9 and FIG. 10). The mortality rate of the contact chickens treated with ΦCJ4 was significantly decreased (P<0.05) when compared with that of the untreated contact chickens. In the re-isolation study, untreated contact chickens displayed a 40% re-isolation rate of the SG challenge strain in the liver and spleen, while the challenge strain was not isolated in contact chickens treated with ΦCJ4 at 2 weeks post-challenge (Table 10).

TABLE 10

Effect of ΦCJ4 on organ invasion caused by horizontal transmission of SG in commercial layers

| | No of chickens | No of chickens with SG re-isolation from organs (%)[A] | | | | | | | | |
|---|---|---|---|---|---|---|---|---|---|---|
| | | 7 pcd[B] | | | 14 pcd | | | 21 pcd | | |
| Group | | Liver | Spleen | Cecum | Liver | Spleen | Cecum | Liver | Spleen | Cecum |
| Group 1 | | | | | | | | | | |
| phage+/SG+ | 15 | 3/5 (60) | 3/5 (60) | 2/5 (40) | 2/5 (40) | 1/5 (20) | 2/5 (20) | 0/5 (0) | 1/5 (20) | 0/5 (0) |
| phage+/SG− | 15 | 0/5 (0) | 0/5 (0) | 0/5 (0) | 0/5 (0) | 0/5 (0) | 1/5 (20) | 0/5 (0) | 0/5 (0) | 0/5 (0) |

TABLE 10-continued

Effect of ΦCJ4 on organ invasion caused by horizontal transmission of SG in commercial layers

| | | No of chickens with SG re-isolation from organs (%)[A] | | | | | | | | |
|---|---|---|---|---|---|---|---|---|---|---|
| | | 7 pcd[B] | | | 14 pcd | | | 21 pcd | | |
| Group | No of chickens | Liver | Spleen | Cecum | Liver | Spleen | Cecum | Liver | Spleen | Cecum |
| Group 2 | | | | | | | | | | |
| phage−/SG+ | 15 | 5/5 (100) | 5/5 (100) | 4/5 (80) | 4/5 (80) | 3/5 (60) | 3/5 (60) | 2/5 (40) | 1/5 (20) | 2/5 (40) |
| phage−/SG− | 15 | 0/5 (0) | 0/5 (0) | 0/5 (0) | 1/5 (20) | 1/5 (20) | 2/5 (40) | 1/5 (20) | 1/5 (20) | 2/5 (40) |
| Negative control | | | | | | | | | | |
| phage−/SG− | 15 | 0/5 (0) | 0/5 (0) | 0/5 (0) | 0/5 (0) | 0/5 (0) | 0/5 (0) | 0/5 (0) | 0/5 (0) | 0/5 (0) |

[A]Number of chickens positive/total number of chickens tested
[B]Day postchallenge In addition, the untreated contact group showed a 40-60% re-isolation rate of the challenge strain in the liver and spleen, while the re-isolation rate in ΦCJ4-treated contact chickens was 20-40% at 3 week post-challenge. Although there were no significant differences in the re-isolation rate of the challenge strain between ΦCJ4-treated and untreated contact chickens, ΦCJ4 treatment reduced the number of chickens colonized with the pathogen after challenge.

[Industrial Applicability]

Having specific bactericidal activity against one or more *Salmonella* bacteria selected from the group consisting of *Salmonella enteritidis* (SE), *Salmonella typhimurium* (ST), *Salmonella gallinarum* (SG), and *Salmonella pullorum* (SP) without affecting beneficial bacteria, in addition to showing excellent tolerance to acid, heat and desiccation, as described hitherto, the novel bacteriophage of the present invention can be widely used as an active ingredient for therapeutic agents, animal feeds or drinking water, cleaners and sanitizers for preventing and treating the infectious diseases caused by *Salmonella enteritidis, Salmonella typhimurium, Salmonella gallinarum* or *Salmonella pullorum* including salmonellosis, *Salmonella* food poisoning, Fowl Typhoid, and *Pullorum* disease.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preventing an infectious disease caused by one or more selected from the group consisting of *Salmonella enteritidis, Salmonella typhimurium, Salmonella gallinarum* and *Salmonella pullorum*, comprising administering an isolated bacteriophage which is deposited under accession number KCCM11027P to a subject in need thereof.

2. The method according to claim 1, wherein the infectious disease caused by *Salmonella enteritidis* or *Salmonella typhimurium* is salmonellosis or Salmonella food poisoning, the infectious disease caused by *Salmonella gallinarum* is Fowl typhoid, and the infectious disease caused by *Salmonella pullorum* is Pullorum disease.

* * * * *